United States Patent
Yun et al.

(10) Patent No.: US 9,539,329 B2
(45) Date of Patent: Jan. 10, 2017

(54) LIGHT-GUIDING HYDROGEL DEVICES FOR CELL-BASED SENSING AND THERAPY

(71) Applicant: The General Hospital Corporation, Boston, MA (US)

(72) Inventors: Seok-Hyun Yun, Cambridge, MA (US); Myunghwan Choi, Cambridge, MA (US)

(*) Notice: Subject to any disclaimer, the term of this patent is extended or adjusted under 35 U.S.C. 154(b) by 0 days.

(21) Appl. No.: 14/516,874

(22) Filed: Oct. 17, 2014

(65) Prior Publication Data

US 2015/0056143 A1   Feb. 26, 2015

Related U.S. Application Data

(63) Continuation-in-part of application No. 14/239,697, filed as application No. PCT/US2012/052451 on Aug. 27, 2012.

(60) Provisional application No. 61/892,535, filed on Oct. 18, 2013, provisional application No. 61/529,570, filed on Aug. 31, 2011, provisional application No. 61/561,191, filed on Nov. 17, 2011.

(51) Int. Cl.
| | |
|---|---|
| *A61K 9/00* | (2006.01) |
| *A61K 47/10* | (2006.01) |
| *A61N 5/06* | (2006.01) |
| *A61K 49/00* | (2006.01) |
| *A61B 5/00* | (2006.01) |

(52) U.S. Cl.
CPC ............ *A61K 47/10* (2013.01); *A61K 9/0024* (2013.01); *A61K 49/0054* (2013.01); *A61K 49/0073* (2013.01); *A61N 5/0601* (2013.01); *A61B 5/0059* (2013.01); *A61N 2005/063* (2013.01); *A61N 2005/0626* (2013.01)

(58) Field of Classification Search
CPC ....................................................... A61K 47/10
See application file for complete search history.

(56) References Cited

U.S. PATENT DOCUMENTS

| | | | |
|---|---|---|---|
| 8,233,953 B2 * | 7/2012 | Colvin, Jr. ............ | A61B 5/0031 600/316 |
| 2013/0211213 A1 * | 8/2013 | DeHennis .............. | A61B 5/076 600/316 |

FOREIGN PATENT DOCUMENTS

WO   WO 2008/100617   *   8/2008

* cited by examiner

*Primary Examiner* — Paul Dickinson
(74) *Attorney, Agent, or Firm* — Yakov Sidorin; Quarles & Brady LLP

(57) ABSTRACT

A hydrogel-lightguide based sensory system susceptible to a stimulus signal produced by ambient and stimulating sensory cells embedded in a hydrogel body of the system. Sensory cells generate an optical signal (in response to a user-defined triggering with excitation light or, alternatively, due to bioluminescence) the properties of which, determined based on detection of such signal with an optical detector device, provide characterization of the stimulus and information required for user-defined activation of emitter cells encapsulated in the hydrogel. When activated, emitter cells generate matter and/or light directed to interact with the ambient.

21 Claims, 13 Drawing Sheets

FIG. 8E
FIG. 8F
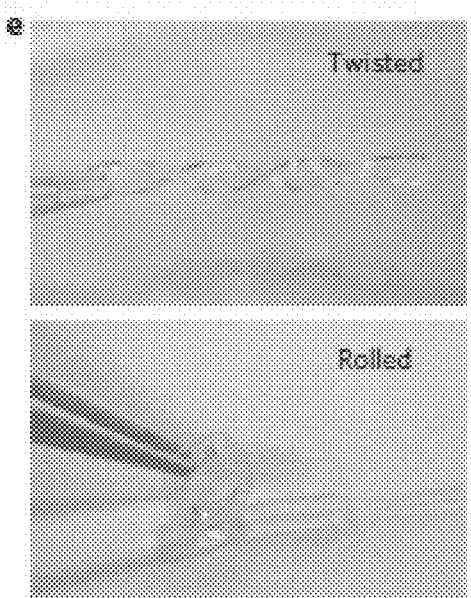
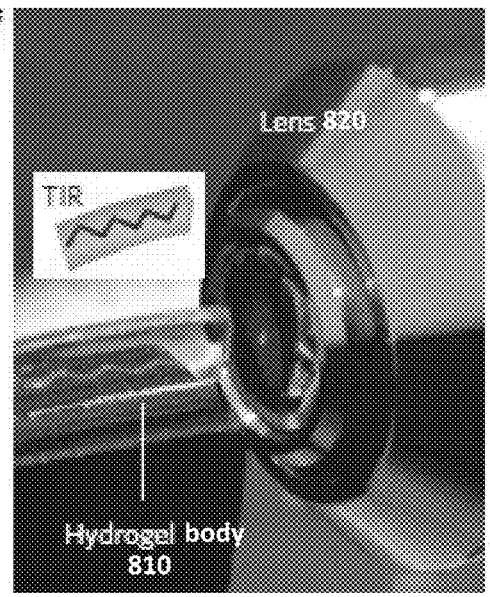
FIG. 8G
FIG. 9A
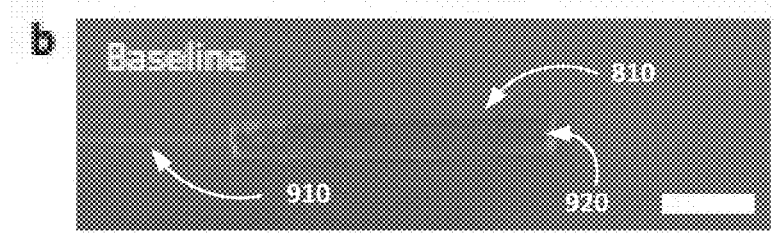
FIG. 9B
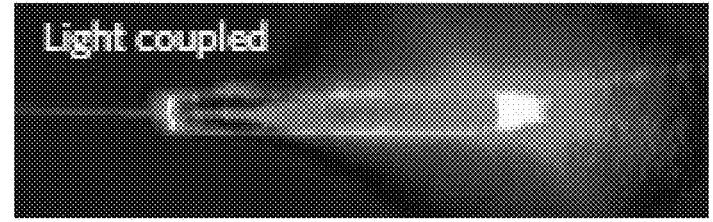
FIG. 9C
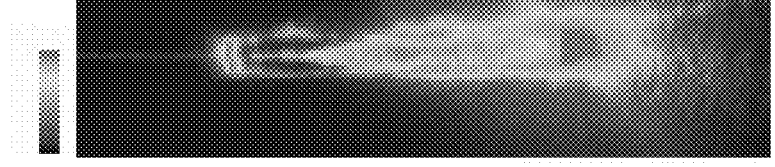

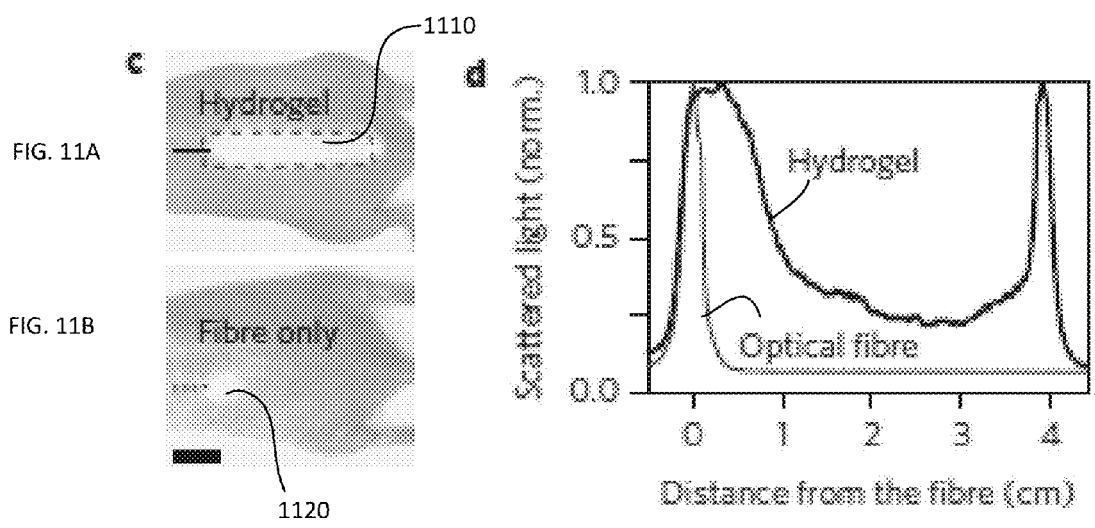
FIG. 11A
FIG. 11B
FIG. 11C
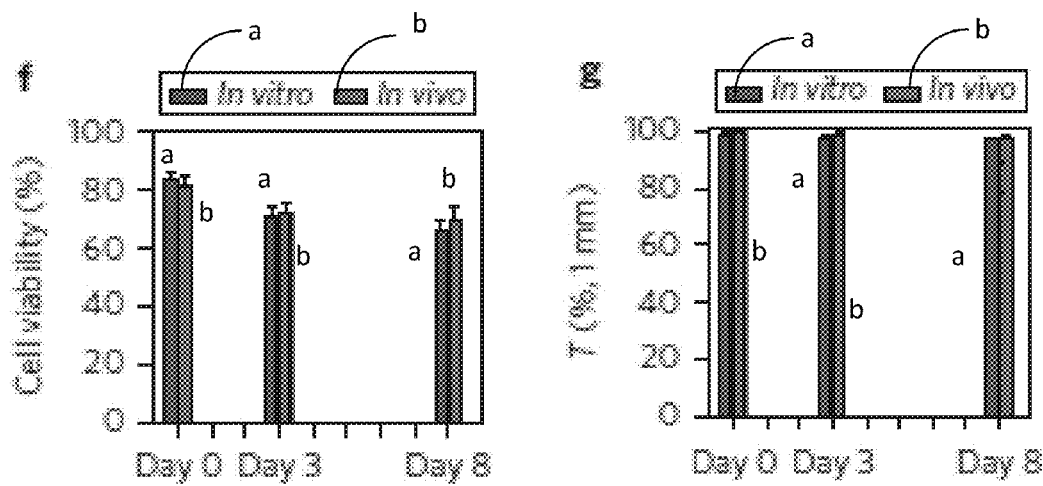
FIG. 11D
FIG. 11E

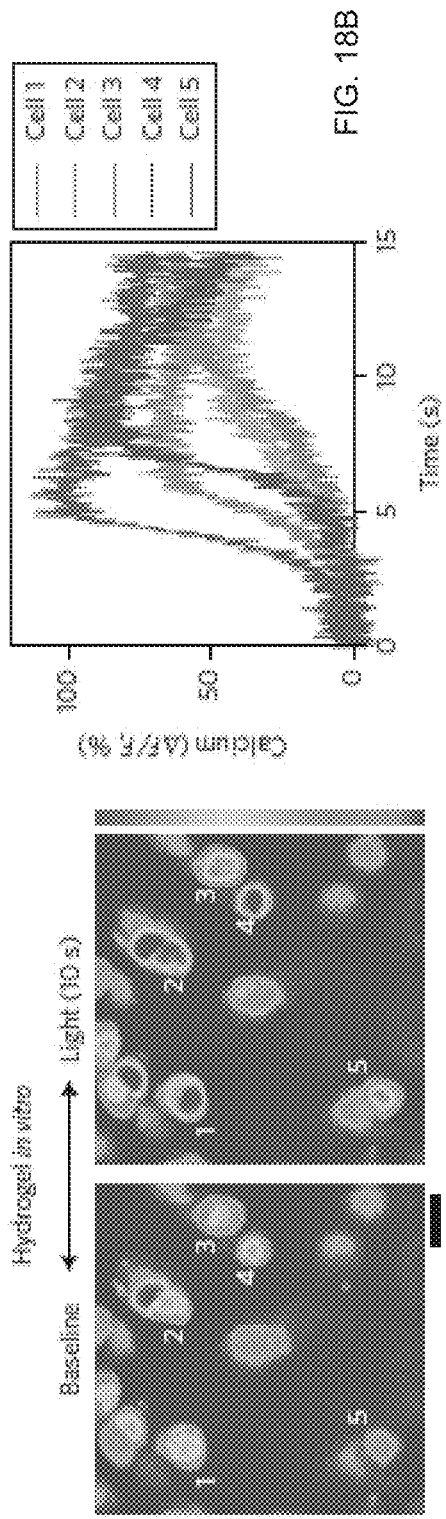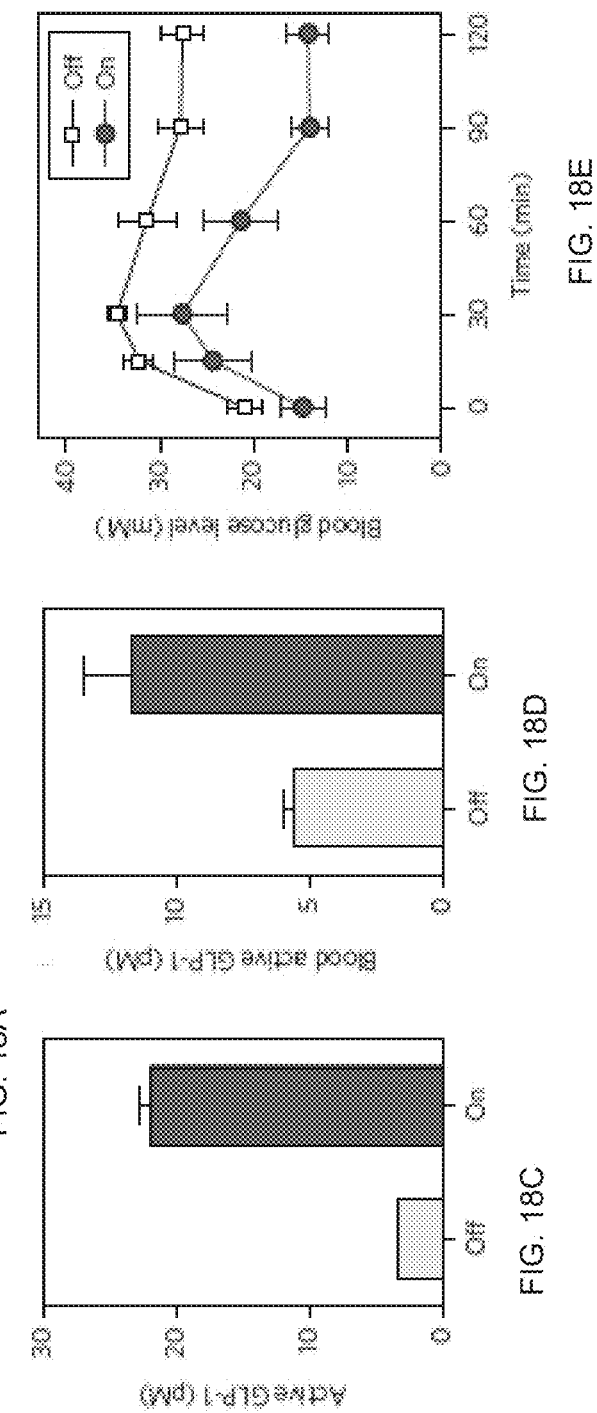
FIG. 18A  FIG. 18B  FIG. 18C  FIG. 18D  FIG. 18E

LIGHT-GUIDING HYDROGEL DEVICES FOR CELL-BASED SENSING AND THERAPY

CROSS-REFERENCE TO RELATED APPLICATIONS

The present patent application claims priority from and benefit of the U.S. Provisional Patent Application No. 61/892,535 filed on 18 Oct. 2013 and titled "Light-Guiding Hydrogel Implants for Cell-Based Sensing and Therapy." The present application is also a continuation-in-part of U.S. patent application Ser. No. 14/239,607 filed on Feb. 19, 2014 and titled "Systems and Methods for Facilitating Optical Processes in a Biological Tissue". The named U.S. patent application Ser. No. 14/239,607 is a national phase of the International Patent Application PCT/US2012/052451 filed on Aug. 27, 2012, which in turn claims priority from U.S. Provisional Patent Applications Nos. 61/529,570 filed on Aug. 31, 2011 and 61/561,191 filed on Nov. 17, 2011. The disclosure of each of the above-identified patent applications is incorporated herein by reference.

STATEMENT REGARDING FEDERALLY SPONSORED RESEARCH OR DEVELOPMENT

This invention was made with Government support under Grant Number EB013761 awarded by the National Institutes of Health, Grant Numbers FA9550-11-1-0331 and FA9550-10-1-0537 awarded by the U.S. Department of the Air Force, and Grant Number 1101947 awarded by the National Science Foundation. The Government has certain rights in this invention.

TECHNICAL FIELD

The present invention relates generally to systems and methods of light delivery to specialized, target cells juxtaposed with or implanted in a living biological tissue and, more particularly, to activation and/or assisting light-based diagnostic and/or therapeutic processes by delivering light into and from the depths of biological tissue with the use of an optically transmissive hydrogel-based system incorporating such target cells.

BACKGROUND

As the autonomous building block of the body, cells are known to have abilities to sense the local ambient environment and respond to external chemical and physical cues. Cells are also known to secret cytokines and hormones that are critical for homeostasis and useful for therapeutic purposes. Efforts have been made to employ these cellular functions for diagnosis and treatment by injecting specialized cells or implanting bioengineered cells in biological tissue, for example in patients. To make use of the cellular functions of so implanted specialized cells, it is often necessary to establish communication with these cells from a distance to be able to send regulatory control signals to the specialized cells or to receive signals, from these cells, that represent the cells' sensory response to the ambient.

Light offers an attractive means of communication with the cells in the biological system. Despite the great promise of light-mediated, cell-based sensing and therapy, there remain challenges that currently available phototherapeutic modalities have not overcome. Such challenges include high optical loss in the biological tissue due to scattering and absorption, a need to dispose the specialized cells in close proximity of the targeted biological tissue, low spatial density with which these specialized cells can be juxtaposed with the biological tissue (which leads to the need to illuminate these cells and collect cells' sensory signals at low intensity levels), and a need to removably bring the source of light (for example, an optical fiber) irradiating the specialized cells in contact with or inside the tissue itself, to name just a few.

There remains, therefore, a need in a methodology that facilitates light delivery into cells implanted in a biological tissue at at least dermatological depths or deeper (in order to, for example, photo-activate light-matter interaction processes in the tissue), that overcomes the abovementioned challenges, and that does not cause trauma associated with a post-irradiation removal of the light-delivery system from the tissue.

SUMMARY OF THE INVENTION

Embodiments of the present invention provide an assembly that includes a polymer hydrogel body and sensory receptors encapsulated inside such body. The sensory receptors are configured when irradiated with first light channeled thereto by said body, to detect a stimulus produced by an ambient in the vicinity of said body when irradiated with first light channeled to the sensory receptors by the body and to emit second light is response to a detection of such stimulus. The body further encapsulates reflex elements therein, which reflex elements are configured (in response to user input applied thereto) to generate an output following emission of the second light by said sensory receptors. Such output includes matter that interacts with the ambient. In a specific case, the sensory receptors are distributed inside the body with spatial density of at least $1*10^6$ cells per cubic centimeter. The polymer hydrogel body has optical transparency that, as a chosen wavelength, increases with increase in molecular weight of a hydrogel contained in the body. In one embodiment, the polymer hydrogel body has mechanical flexibility that increases with increase in molecular weight of a hydrogel contained in the body. In a specific case, the assembly is configured to have scattering-induced attenuation of light propagating therethrough that is increases non-linearly with increase of spatial density of the sensory receptors encapsulated within the body. In a specific embodiment, the reflex elements may be configured to generate the output only when irradiated with third light delivered thereto through the polymer hydrogel body.

At least one of a source of light and an optical detection unit may be disposed in optical communication with polymer hydrogel body via, for example, an optical waveguide. The assembly may be further equipped with a programmable processor operably that is connected with such source of light and such optical detection unit and that is configured to govern operation thereof. In one specific case, the source of light is embedded in said polymer hydrogel body.

The assembly may additionally include programmable electronic circuitry configured to cause generation of (i) the first light by a source of light and (ii) data, representing a characteristic of the stimulus based on second light received by an optical detection unit, where the source of light and optical detection unit are disposed outside of the polymer hydrogel body in optical communication with both sensory receptors and reflex elements.

Embodiments of the invention additionally provide a method for operating an assembly. The method includes: (i) transmitting first light through a polymer hydrogel body, of the assembly, to activate sensory receptors encapsulated in said body to render said sensory receptors sensitive to a stimulus produced outside said polymer hydrogel body; (ii) detecting second light, generated by activated sensory receptors in response to the stimulus, with an optical detection unit of the assembly; and (iii) generating an output with reflex elements encapsulated within the polymer hydrogel body, such that the output includes one or more of a molecular output and a photon output. The step of transmitting may include guiding the first light (which has been externally delivered to the hydrogel body) within the body. Alternatively or in addition, the step of transmitting may include transmitting first light through the polymer hydrogel body that has been subcutaneously implanted into a biological tissue and/or transmitting light through a polymer hydrogel body that has absorption, of said light, which is non-linearly dependent on a spatial density of the first cells encapsulated in the body. Alternatively or in addition, the method may include transmitting at least one of the stimulus and second light through the body.

Alternatively or in addition, the method may includes defining optical transmittance of the polymer hydrogel body by varying molecular weight of a polymer hydrogel contained therein; and/or comprising delivering the second light to a detector outside of the tissue (where the transmitting includes transmitting first light delivered to the body from a light source disposed outside of the tissue). In one embodiment, the step of generating includes generating second light in response to a stimulus produced by an ambient biological medium exposed to toxic environment, such generating including generating second light indicative of the presence of an antidote in the toxic environment. The method may further include a step of transmitting the output outside of the polymer hydrogel body.

BRIEF DESCRIPTION OF THE DRAWINGS

The invention will be more fully understood by referring to the following Detailed Description in conjunction with the generally not-to scale Drawings, of which:

FIGS. 8E, 8F illustrate mechanical flexibility of the PEG hydrogel (5 kDa, 10%);

FIG. 8G and insert provides an illustration to the total-internal-reflection of light at 491 nm within the slab hydrogel body;

FIGS. 9A, 9B, and 9C provide illustrations of light coupling to a hydrogel body. FIG. 9A: a hydrogel body before light coupling; FIG. 9B: light guiding by the hydrogel body and outcoupling through a distal end; FIG. 9C: a pseudo-color image of the spatial profile of the scattered light;

FIG. 11A is a diagram showing a light-scattering profile associated with a fiber-optic pigtailed embodiment of a polymer hydrogel body used as an implant in a biological tissue;

FIG. 11B is a diagram showing a spatial profile of light emitted from a fiberoptic pigtail of FIG. 11A (without a hydrogel body attached to it)

FIG. 11C is a plot illustrating longitudinal profiles of light scatted from the hydrogel body of FIG. 11A and only optical fiber of FIG. 11B;

FIG. 11D is a bar-chart illustrating long-term viability of encapsulated cells in vivo. Error bars are standard deviations (n=6 each);

FIG. 11E is a bar-chart illustrating change in optical transmittance of the hydrogel body implants in vivo;

FIG. 12A: Fluorescence images of the hsp-70-GFP sensing cells in vitro. FIG. 12B: Dose-dependent activation of GFP (green fluorescent protein) fluorescence. FIG. 12C: Phase contrast images and corresponding fluorescence images of the sensing cells in a hydrogel at 24 hours after CdCl2 was added to the medium. FIG. 12D: Dose-dependent activation of GFP signal in vitro;

FIG. 17A: Western blot analysis confirming the expression of melanopsin. FIG. 17B: Two fluorescence calcium-level images representing cells before and after illuminating blue light (10 s), respectively. The cells were preloaded with a fluorescent calcium indicator. FIG. 17C: Time traces of the calcium signals in various cells. FIG. 17D: The GLP-1 level in the cell media measured by ELISA before and after illuminating blue activation light;

FIGS. 18A, 18B, 18C, 18D, 18E illustrate results of an experiment on optogenetic therapy in a mouse model of diabetes. FIG. 18A: two images illustrating fluorescence calcium-level imaging of optogenetic cells in a hydrogel waveguide in vitro. Upon delivering blue light (455 nm) through the fiber for 10 s at 1 mW, a fluorescence signal from an intracellular calcium indicator (OGB1-AM) increased; Scale bar, 20 mm. FIG. 18B: Time traces of intracellular calcium signals from various cells (indicated in FIG. 18A). FIG. 18C illustrates concentrations of active GLP-1 in the medium of hydrogels with (on) and without (off) activation light. FIG. 18D shows a level of GLP-1 in blood plasma measured in vivo at 2 days after light exposure. FIG. 18E presents blood glucose levels in chemically induced diabetic mice with and without activation light. Error bars, standard deviations (n=4);

Figure 1:
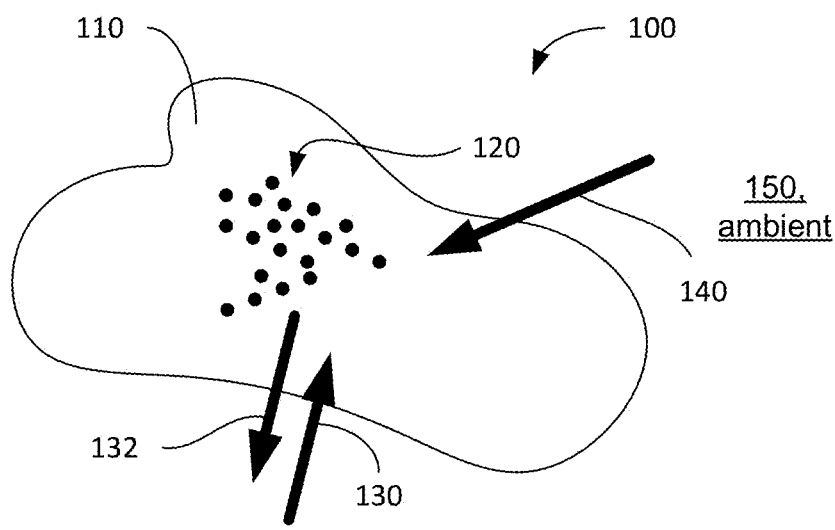
FIG. 1 is a general diagram of a polymer hydrogel body of an embodiment of the invention.

Generally, the sizes and relative scales of elements in Drawings may be set to be different from actual ones to appropriately facilitate simplicity, clarity, and understanding of the Drawings. For the same reason, not all elements present in one Drawing may necessarily be shown in another.

DETAILED DESCRIPTION

The field of light-mediated, cell-based sensing and/or therapy continues to evolve. One of limitations curtailing these development remains the high loss of light (directed at the target specialized cells juxtaposed in fluid communication with the ambient such as a biological tissue) due to scattering and absorption in the ambient.

The so-called 1/e optical penetration depth, $L_e$ (at which the light intensity drops to 1/e level or about 37%) in soft tissue is less than 1 mm for the visible and near infrared range. In attempt to overcome this imitation, several approaches have been employed. Transdermal light delivery by external illumination, for example, has shown to be viable for an optogenetic release of a therapeutic protein from the cells implanted into the tissue subcutaneously. While this approach is feasible in small experimental animals such as mice through their thin skin, its application to humans is not particularly feasible because it would require the application of too high optical energy levels, beyond the safety threshold (~4 W/cm$^2$) of the tissue. Minimally invasive access into the body and, therefore, direct light delivery to the target, specialized cells can be provided by endoscopes. But this approach limits the location of target cells to near the surfaces of internal organs (such as, for example, the mucosal layer of the gastrointestinal tracts) that have to be affected by the response of the target cells to the delivered irradiation, and is not suitable for continuous operation over an extended period of time (e.g. several days).

Yet another problem with existing methodologies is the need to illuminate the implanted targeted cells and collect light from them when the cells are dispersed widely in space. Indeed, while a point-source illumination o the target cells (with light delivered through an optical fiber, for example) is adequate for certain scenarios, such as focal optogenetic control in the brain, most applications demand a sufficient number of cells distributed over distances that are much larger than the typical 1/e optical attenuation distance on order of 1 mm, for which point illumination by conventional optical fibers is not suited.

The idea of the present invention stems from the realization that changes occurring in the ambient (and, in particular, in a biological tissue) can be detected with the use of an assembly or device containing judiciously chosen sensory elements that are disposed in fluid communication with the ambient and the sensitivity of which to such changes is activated or triggered as a result of interaction between the sensory receptors and appropriately chosen radiation. Such configuration is advantageous in that is allows the sensory system of the assembly be controlled at the user's discretion. The idea of the present invention is further rooted in the realization that the changes occurring in the ambient can be counteracted or at least affected by producing, with reflex elements of the assembly, a judiciously defined output affecting the ambient.

The terms "sensory receptors", "target specialized cells", "sensor cells", and "first cells", which may be used interchangeably herein, are used to denote a group of probing or sensing elements configured to produce an optical output (as a non-limiting example—fluorescence, luminescence) in response to being exposed to an environmental (ambient) stimulus. In one implementation, the sensory receptors generate light output (for example, in the form of fluorescence) only when irradiated with light and interact with the stimulus produced by the ambient. The characteristics of light generated by the sensory receptors provides an indication of characteristics of the stimulus. In another implementation, the sensory receptors are configured to generate light output (for example, in the form of bioluminescence) when brought in contact with the stimulus and without additional triggering irradiation. The stimulus may include a change in a chemical composition associated with an ambient environment (for example, emission of cytokines and/or hormones by the biological tissue). The terms "a reflex element", "a reflex cell", and "a second cell" are used herein interchangeably to refer to an element that, in response to being irradiated with light at a wavelength to which such element is sensitive, produces a physical or chemical output (in the form of a molecular output or a photonic output) which, in a specific case, is configured to produce a counterbalancing effect on the environment to compensate for a cause of generation of the stimulus.

Both the sensory receptors and reflex elements may be housed or encapsulated in an optical system that is juxtaposed against the ambient (such as a hydrogel housing structure within which the sensory cells and the reflex cells are dispersed with required spatial density) and that is configured to operate not only as a sensor of the tissue's signals but as a tissue (de)activator in response to such signals as well.

Little, if any, attention has been paid to photonic functionalities of polymer hydrogels in context of biomedical applications and to ways of structuring them as self-contained hydrogel cell-based biologically-compatible optical transceivers configured to operate in contact with living biological tissue while sensing the activating agent(s) released by the living biological tissue and generate optical response to such activating agent(s). According to the idea of the invention, the activating agent(s) or stimulus (such as a chemical composition or a change in a chemical composition associated with the tissue) produced by the tissue in response to some cause or interrogation (the presence of which is of interests) are processed with the use of photonic modality of a polymer-hydrogel-based assembly of the invention, the properties of which are appropriately chosen and tuned, to generate a physical and/or chemical response which, when passed to the tissue, redresses or offsets that cause.

EXAMPLES OF EMBODIMENTS

Example 1

As shown schematically in FIG. 1, an embodiment 100 of the assembly of the invention includes, in part, a light-collecting three-dimensional body 110 containing a polymer hydrogel material that encapsulates sensory receptors or cells 120. The body 110 may be structured in various fashions, for example as a slab waveguide or a thin-film waveguide discussed in U.S. patent application Ser. No. 14/239,607; or as a 3D body having a different shape. In a specific case, when the polymer hydrogel body 110 is configured as a lightpipe (for example, a rectangular flexible slab with dimensions on the order of several mm by a millimeter by several tens of millimeters), it may include an optical-lightguide core and/or cladding (as known in the art; not shown in FIG. 1) that facilitate light-guiding within the body. The optical index distribution in such lightguide has a predetermined profile judiciously chosen to facilitate guiding of light 130, 132 for delivery of light to and/or from a predetermined light collector (to be discussed below). In one specific case, the distribution of refractive index in a slab-like polymer hydrogel body has a graded profile with the higher index near the center of the slab. The sensory receptors 120 are configured to be activated (for example, with light 130 delivered to the body 110) to render these receptors susceptible to a physical or chemical stimulus 140 transmitted to the receptors 120 from the ambient 150 through the body 110. The receptors 120 may be disposed inside the body 110 with different spatial densities, as discussed below, and may be disposed in a localized fashion and spatially non-uniformly throughout the body 110 or, alternatively, impregnate and saturate it. An implementation of the polymer hydrogel body 110 can be fabricated by controlling a spatial index profile of a precursor, light exposure, and/or water intake. The refractive index distribution may be controlled by changing the chemical composition of the precursor, or the molecular weight of the hydrogel, its cross-linking density, and/or polymer concentration as known in the art.

Figure 2:
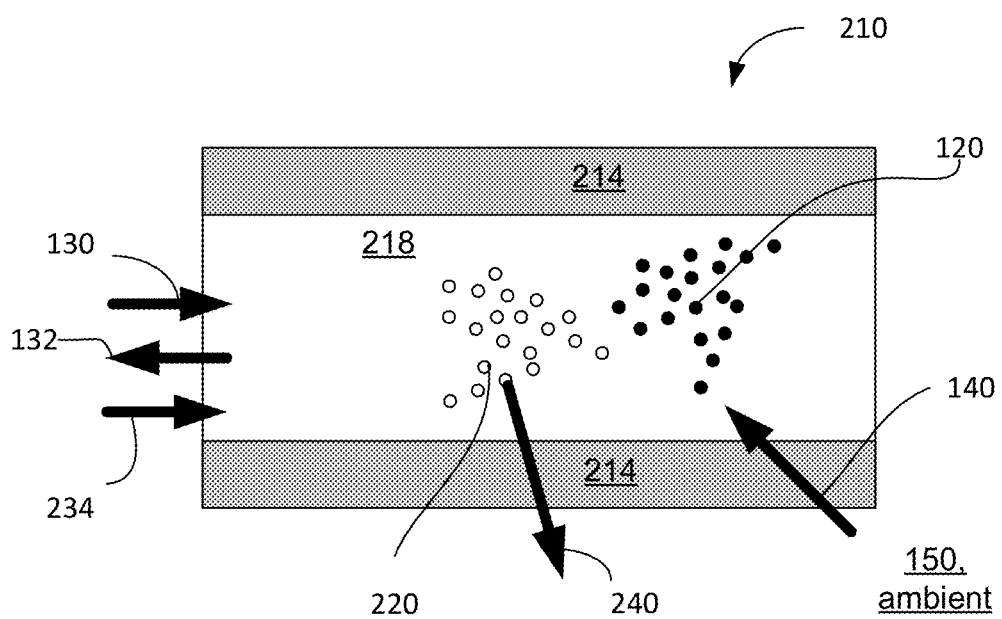
FIG. 2 is a diagram of a specific implementation of a polymer hydrogel body.

In addition, a hydrogel body of the embodiment, shown as element 210 in FIG. 2 (this time structured as a lightguide having a core 214 and a cladding 218) may include reflex elements 220 the operation of which is activated with light 234 delivered to these elements through the body 210. While the elements 220 are shown grouped together and separated from the sensory receptors 120, it is understood that the spatial distribution of the elements 120, 220 in the hydrogel body 210 (or 110) can be predeterminately arranged. In one non-limiting example, the elements 120, 220 can be intermixed throughout the body 210 (or 110) such that at least one of the elements that are immediately neighboring to a given element 120 is the element 220. In one embodiment, the reflex elements 220 may be configured to be activated by light 232 delivered/guided through the hydrogel body 210, 110 and, in response to being irradiated with such light, produce an output 240 (in a form of releasing a molecular substance or light) that is further transmitted through the body 210, 110 to the ambient 150.

In a specific example (when an embodiment of the invention is configured to operate in direct contact with the living tissue, for example to be implanted subcutaneously), the hydrogel body 110, 210 is made biocompatible to avoid severe immune response by the host tissue and, optionally, to support viable cell culture inside the hydrogel. In such application, the sensory receptors 120 and/or reflex elements 220 may be engineered genetically or chemically to effectuate diagnostic and/or therapeutic functions mediated by light 130, 234. Genetic engineering may include insertion of photo-active proteins (such as rhodopsin, melanopsin, for example) to render light-responsiveness; insertion of an optical reporter gene (such as fluorescent protein, bioluminescent protein, for example) for sensing of the stimulus 140; and synthetic engineering of downstream cellular signaling for generating desired cellular behavior (such as secretion of therapeutic proteins, for example).

Figure 3:
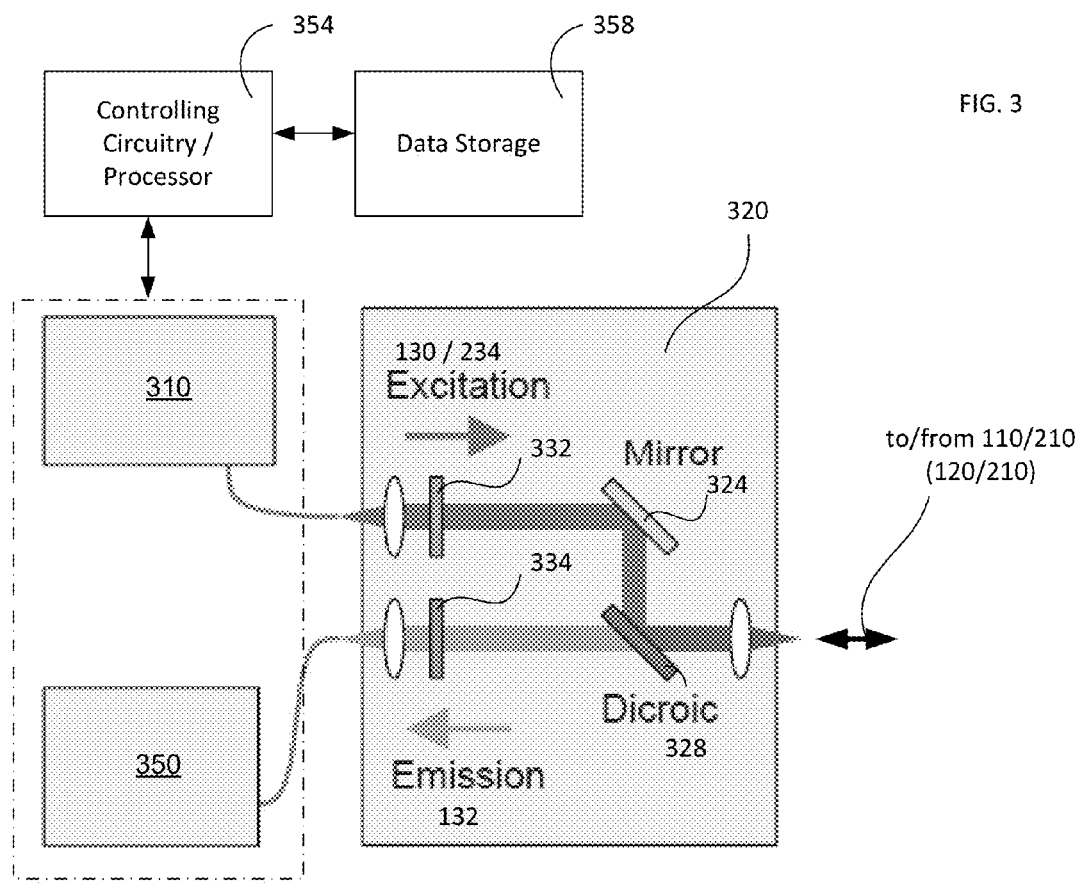
FIG. 3 is a diagram illustrating a portion of an optoelectronic assembly according to an embodiment of the invention.

To effectuate light delivery to and from the sensory receptors and/or the reflex elements from outside of a hydrogel body, an opto-electronic scheme illustrated in FIG. 3 can be employed. Here, the excitation light (130 and/or 234, at a single wavelength or polychromatic, depending on specific optical properties of the elements 120, 220) is generated by an external light source 310 (which may include light emitting diode(s), laser(s), or another appropriate source of light) and delivered through a conventionally-structured optical (de)multiplexing system 320 towards the 110/210 (in one embodiment—through an optical fiber; not shown). The system 320 may include optical reflectors and/or beamsplitters 324, 328; spectral filters 332, 334; and other appropriate optical elements such as lenses required for relay of light. Light 132, collected from the elements 120, 220 within the hydrogel body 110, 210 is delivered in the opposite direction—through the system 320 towards the optical detection device 350 that includes a photo-detector. In response of detecting light 132, the device 350 is configured to produce data indicative of characteristics of light 132. In one implementation, the device 350 may include a spectrophotometer.

For example, a fiber-coupled LED 310 generating light 130 in a spectral band around 455 nm for excitation of the sensory receptors 120 (such as melanopsin, channelrhodopsin, for example) may be used. Upon irradiation with the excitation light 130, delivered through the pigtail fiber (not shown) to the hydrogel body 110, these receptors, in the presence of stimulus 140 received from the ambient 150, generate fluorescence in the spectral band between about 500 nm and 550 nm registered by the photodetector of the device 350 as light 132.

Figure 4:
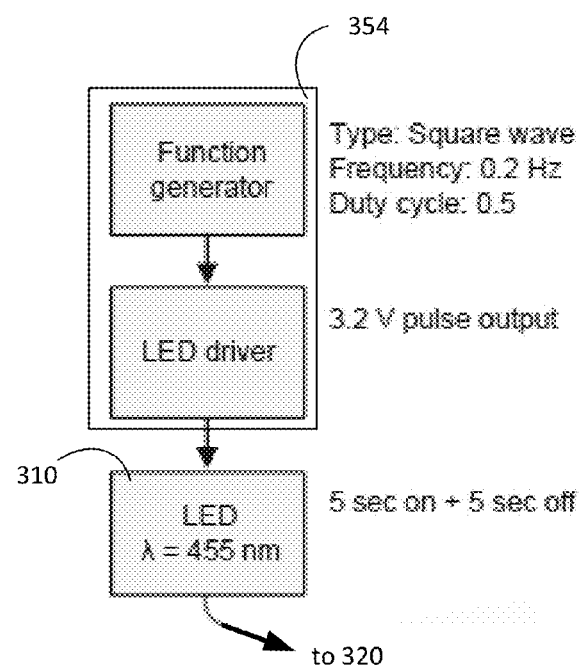
FIG. 4 depicts a specific example of operation of the source of light configured to generate light for excitation of sensory receptors encapsulated in an embodiment of a polymer hydrogel body of the invention.

Generally, the source-detector unit is operably communicated with a controlling circuitry and/or a processor unit 354, which is coupled with a tangible data storage 358 and is specifically programmed to analyze data collected from the optical detection device 350 and generate an electric output triggering the controlling circuitry to govern the operation of the light source 310 and/or the optical detection device 350. FIG. 4 illustrates a specific example of an operational mode of the controlling circuitry 354.

Example 2

Figure 5:
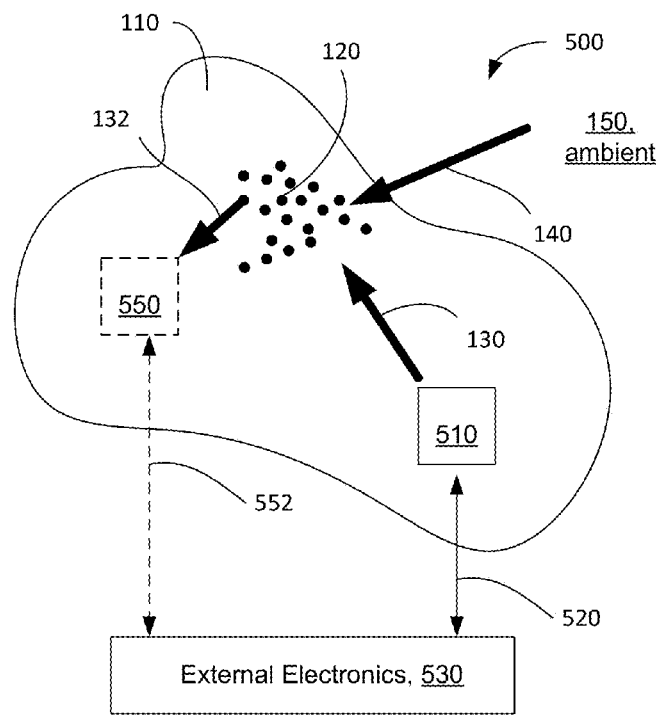
FIG. 5 is an embodiment with a polymer hydrogel body incorporating at least a source of excitation light, driven by and operably cooperated with external circuitry via a wireless connection.

According to idea of the invention, at least a light source used for excitation of the elements 120 and/or 220 (or, possibly, both such a light source and an optical detector configured to register the optical response of the sensory receptors to the excitation light) may be integrated within the hydrogel body 110, 220. A hydrogel body 110 of the embodiment 500 of FIG. 5, for example (for simplicity shown to encapsulate only the sensory receptors 120) includes a light emitter 510 structured to be powered by an external energy source 514 via a wireless connection 520, for example by induction coupling from the transmitter of the external electronic circuitry 530. In one specific example, a single micro-LED (such as that described by R. Mandal et al. in "*Wirelessly Powered and Controlled, Implantable, Multi-channel, Multi-wavelength Optogenetic Stimulator*"; 2013 IEEE MTT-S International Microwave Workshop of RF and Wireless Technologies for Biomedical and Healthcare Applications, IMWS-BIO; the disclosure of which is incorporated herein by reference) or an array of micro-LEDs (for illumination over a larger area) can be encapsulated into the hydrogel body 110. In an embodiment where a micro-photo-detector 550 is also embedded into the body 110, such detector is also set-up to exchange data with and be driven by an external circuitry via a wireless connection 552. The operation of the embodiment 500 may require the use of at least a part of the embodiment of FIG. 3.

Example 3

Figure 6:
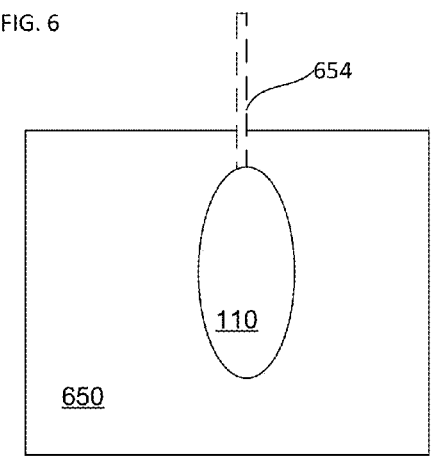
FIG. 6 is a diagram illustration the formation of a hydrogel body in the ambient medium via a gelation process.

In one implementation, schematically illustrated in FIG. 6, the hydrogel body 110 is formed inside the biological tissue 650 via injection of a liquid-phase material through a small-diameter injector 654 and in situ gelation following the injection. In one example, such material may include PEG-PLGA-OEG triblock copolymer, designed to be in a liquid phase at temperatures that are lower than the body temperature and initiate gelation at about 37° C. The injector is removable (as shown by a dashed line) and, in practice, is disposed of after the gelation of the body 110 with at least one of the sensory receptors and reflex elements encapsulated in it.

Example 4

In a related embodiment, discussed herein in reference to FIGS. 1, 3 and 6, it is recognized that the implanted in or formed within the tissue hydrogel body can be configured from a material made biodegradable (for example, via hydrolysis or enzymatic degradation) or photodegradable (via the addition of appropriate photo-linkers such as photodegradable acrylate and host linker such as PEG-diacrylate (see, for example, A. M. Knoxin et al., "*Photodegradable Hydrogels for Dynamic Tuning of Physical and Chemical Properties*", Science, vol. 324, Apr. 3, 2009; available at www.sciencemag.org; the disclosure of which is incorporated herein by reference). As a result, the body 110,210 is configured to degrade either gradually at its own pace or upon a triggering input (such as irradiation at an appropriate wavelength) applied to the hydrogel body. For biodegradable gels, the degradation kinetics may be optimized with respect to the desired life-time of the hydrogel body. In case of a photo-degradable gel, it is preferred that operable parameters of degradation-triggering irradiation differ from the parameters of excitation/emission (130, 234/132) light.

Example 5

Figure 7:
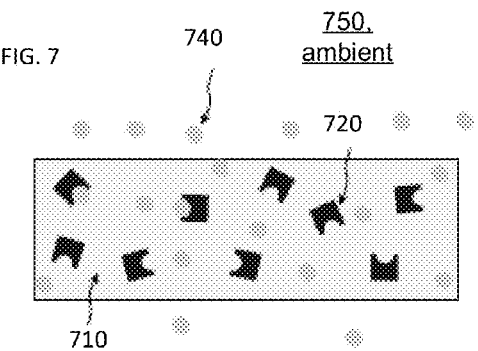
FIG. 7 is a diagram showing an embodiment employing sensory receptors configured as sources of bioluminescence.

In a related implementation, a portion of which is shown in FIG. 7, and in further reference to FIG. 3, the hydrogel body (such as the body 110, 210, for example) placed in direct contact with the ambient tissue 750 can be structured to encapsulate a self-powered source of light 710. The self-powered source of light 710 may include a bioluminescent unit that emits light when an appropriate enzyme (as part of a stimulus 740 produced by the tissue 750) interacts with the substrate of the bioluminescent unit. For example, elements of luciferin 720 can be used as bioluminescent sensory receptors, encapsulated inside the body 710, while luciferase is (optionally systemically) introduced into the living tissue. Due to high its diffusivity, luciferase reaches the hydrogel body 710 due to diffusion and, upon interaction with the luciferin, the elements 720 emit bioluminescence guided by the hydrogel body 710 towards the external detection unit (as discussed, for example in reference to FIG. 3). Different variants of luciferin/luciferase are available for operation indifferent spectral regions, from visible to near-IR.

Example 6

In a related embodiment (in reference to FIGS. 1, 2, 3), the encapsulated into the hydrogel body 110 elements 120, 220 may include judiciously-chosen fluorescent chemical compositions instead of biological cell (for use as sensory receptors 120) to ease the fabrication process and to enhance the life of the embodiment. The embedded chemical sensory receptors are configured to change their optical properties (such as parameters of fluorescence, scattering, reflectance, absorbance) in response to a change in physiological or pathological environment in the vicinity of the hydrogel body. In one example, a sensory receptor includes a fluorescent glucose sensor such as boronic acid-based glucose sensor (see T. Kawanishi et al., "*A Study of Boronic Acid Based Fluorescent Glucose Sensors*", J. of Fluorescence, Vol. 14, no. 5, September 2004; the disclosure of which is incorporated herein by reference) configured to emit fluorescent light indicating a change in or level of glucose in the blood of the tissue with which the hydrogel body is in contact. A reflex element 220 can be configured to include a caged molecule as a photoreactive therapeutic agent that is inactive in the default state, but is activated, when irradiated with light 234, to release drug towards the tissue (in one example, caged anticancer drugs from gold nanoparticles; see Sarit S. Agasti et al., "Photoregulated Release of Caged Anticanser Drugs from Gold Nanoparticles", J. of Amer. Chem. Society, vol. 131, pp. 5728-9; communications published on web Apr. 7, 2009; the disclosure if which is incorporated herein by reference)

Example 7

In a specific embodiment, the hydrogel body 110 can be structured as a network of lightguides discussed in U.S. patent application Ser. No. 14/239,607 in reference to FIGS. 1 through 5 therein, and used in conjunction with the external optoelectronic assembly of FIG. 3.

Fabrication and Characterization of a Polymer Hydrogel Body.

Various embodiments of the PEG-based hydrogel body of the invention were formed by UV-induced polymerization and crosslinking of PEG diacrylate (PEGDA) precursor solutions mixed with photoninitators (Irgacure, 0.05% w/v). In particular, a 10%-60% (w/v) solution of PEGDA (available from Laysan Bio) in PBS was mixed with 0.05% (w/v) photoinitiator Irgacure 2959 (Ciba). For cell (sensory receptors/reflex elements) encapsulation, cells were trypsinized, quantified and mixed into the solution at concentration of $1 \times 10^6$-$5 \times 10^6$ cells/ml. The solution with encapsulated cells was transferred to a custom-made glass mold to form a precursor. The so-prepared precursor was fiber-pigtailed with a multimode optical fiber (~100 μm-core, 0.37 NA; available from Doric Lenses), imbedded in the polymer solution and aligned to its longitudinal axis.

The precursor was then irradiated with light from an UV lamp (365 nm, 5 mW/cm$^2$; Spectroline) for 15 min for photocrosslinking. The resulting cell-encapsulating hydrogel was transferred to culture medium and incubated. The medium was replaced at 1 h, 3 h, and every 24 hours.

Optical Transparency of PEG Hydrogels.

Figure 8A:
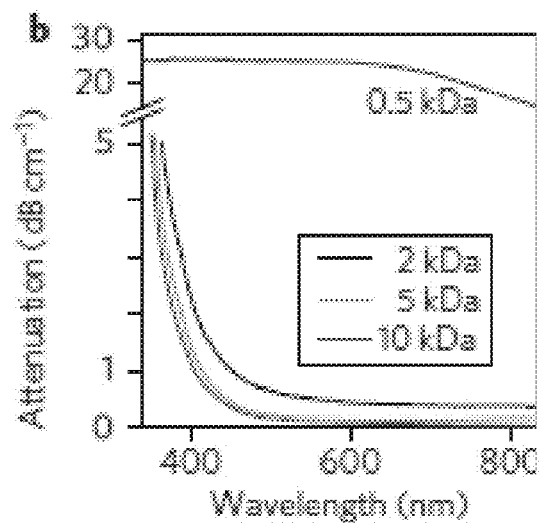
FIG. 8A shows optical attenuation spectra of PEG hydrogels prepared with different molecular weights of PEGDA.

To determine the optimal compositions of the hydrogels, optical loss spectra of hydrogels prepared using PEGDA with various molecular weights (0.5, 2, 5 and 10 kDa) but at the same concentration (10% wt/vol) were measured, FIG. 8A. PEG hydrogels with a molecular weight of 0.5 kDa in standard 1 cm cuvettes were white and opaque, which indicated high level of uniform scattering across the visible spectrum. The fabricated 0.5 kDa hydrogels (10% wt/vol) were semi-opaque when viewed through the 1 mm thickness, whereas the 5 kDa hydrogels were markedly more transparent.

With increasing molecular weight, the transparent of the PEG hydrogels was increasing. The spectroscopic measurement of attenuation confirmed a strong dependency of attenuation on molecular weight of the precursor polymer. PEG hydrogels of 0.5 kDa had an optical loss of about 25 dB cm$^{-1}$ ($L_e$=1.8 mm) in the visible range (400-700 nm). When the PEGDA concentration was increased to 60% wt/vol or higher, the hydrogels became noticeably more transparent. However, these concentrations were not adequate for cell encapsulation because of the low water content (<90%). Furthermore, the hydrogels became increasingly stiffer with the increase of concentration, which, in operation, can reduce viability of encapsulated cells and cause undesirable tissue damage when implanted in vivo. Hydrogel bodies prepared with 2, 5 and 10 kDa PEGDA exhibited much lower optical loss.

Figure 8D:
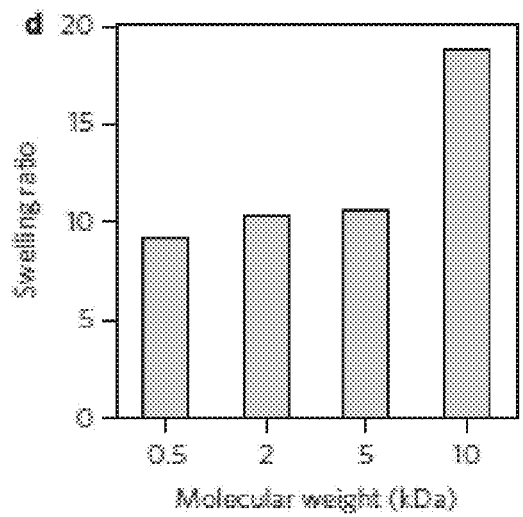
FIG. 8D is a bar diagram illustrating swelling ratios of embodiments of PEG hydrogel bodies. The swelling ratio was calculated by dividing the weight of swollen hydrogel by the weight of dried hydrogel (n=3)
Figure 8B:
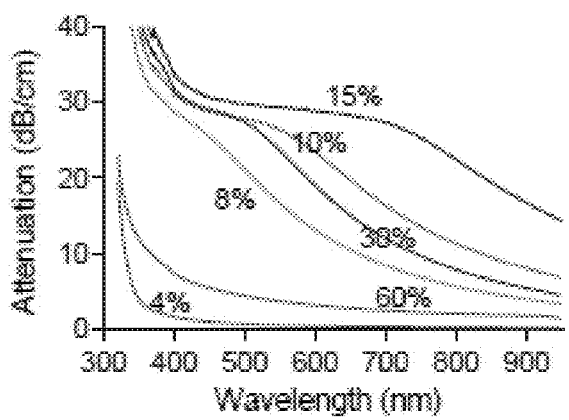
FIGS. 8B, 8C provide additional illustrations for optical attenuation spectra and attenuation coefficients (averaged over a spectral range of 450-500 nm) of polymer hydrogels used in embodiments of the invention.
Figure 8C:
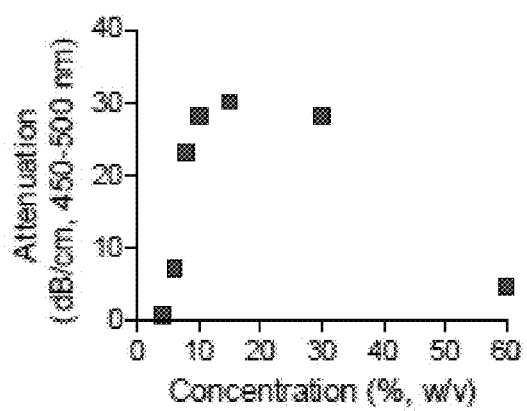

In the blue to green wavelength range (450-550 nm), the average loss was measured to be 0.68 dB cm$^{-1}$ ($L_e$=6.4 cm) for 2 kDa, 0.23 dB cm$^{-1}$ (Le=19 cm) for 5 kDa and 0.17 dB cm$^{-1}$ (Le=26 cm) for 10 kDa PEGDA hydrogels, as shown in FIGS. 8B, 8C. The typical dimensions of the formed PEG hydrogel parallelepipedonal bodies were about 4 mm (width) by about 1 mm (height) by 10-to-40 mm (length).

Effects of Swelling on Physical Properties of a Hydrogel Body.

To mimic the aqueous environment for operation in which the hydrogel bodies are configured and to investigate the stability of the optical properties of the hydrogels, a swelling test was performed. The hydrogels were immersed in phosphate buffered saline (PBS) for 12 h, and the fractional weight increase due to water absorption was measured. The swelling ratio increased with the PEGDA molecular weight increasing from 0.5 to 10 kDa, as shown in FIG. 8D. The shape of the 10 kDa hydrogels was found to be severely deformed due to swelling, whereas 0.5-5 kDa hydrogels maintained their rectangular shapes with minimal distortion. Notably, despite the swelling, all the hydrogels (0.5-10 kDa) showed no apparent changes in transparency. The hydrogels were found to become more flexible with increasing molecular weight. Although 0.5 kDa hydrogels were quite brittle, 5 kDa hydrogels were highly elastic and could easily be bent and twisted (FIGS. 8E, 8F). The study described below utilized PEG hydrogels with 5 kDa molecular weight and 10% wt/vol concentration, in view of their excellent transparency, structural stability and mechanical flexibility.

Light Guiding in Slab Hydrogels

For investigation of optical-guiding properties, rectangular slab hydrogel bodies 510 with dimensions of 4 mm (width)×1 mm (height)×40 mm (length) were chosen, FIG. 8G. The insert of FIG. 8G illustrates total internal reflection of light at about 491 nm launched into the body 510 through a leans 520. The refractive index of 10% wt/vol hydrogels was estimated to be about 1.35 (the index of 100% PEG is 1.465). In reference to FIG. 9A, through a multimode optical-fiber pigtail 910 (core diameter, 100 mm; numerical aperture 0.37) integrated during fabrication with the hydrogel body 810, light from an external light source was coupled into the hydrogel using the set-up of FIG. 3. Light delivered by the optical fiber 910 was dispersed in the cross-section of the hydrogel body 810 nearly uniformly after several-millimeters of propagation, FIG. 9B. The light was guided by the 4 cm long hydrogel body all the way to the distal end 920 and emitted through the end surface of the distal end, FIG. 9C.

Light Collection by Hydrogel Bodies.

Figure 10A:
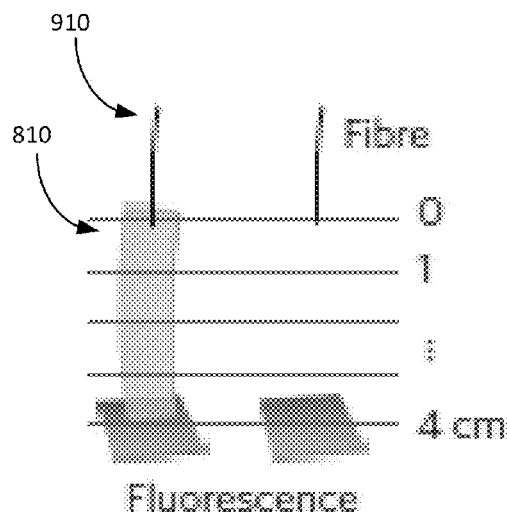
FIG. 10A is a diagram of an experimental set-up for measuring light-collection efficiency. A fluorescent sample was placed in contact with hydrogel bodies of different lengths and at equivalent distances from a multimode fiber.
Figure 10B:
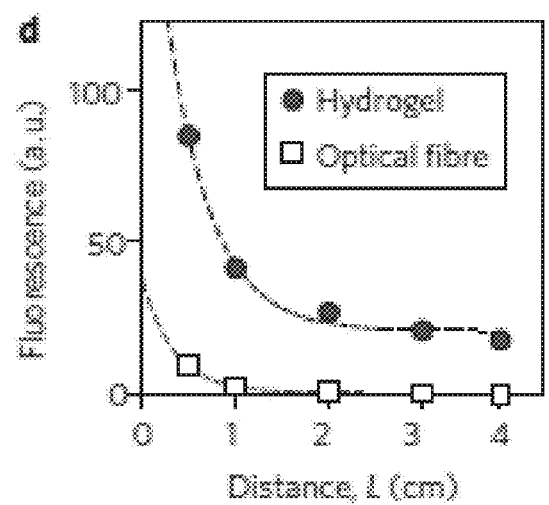
FIG. 10B is a plot demonstrating experimentally-determined amount of fluorescence collected delivered to a photodetector through an optical fiber of FIG. 10A with and without a hydrogel body.
Figure 10C:
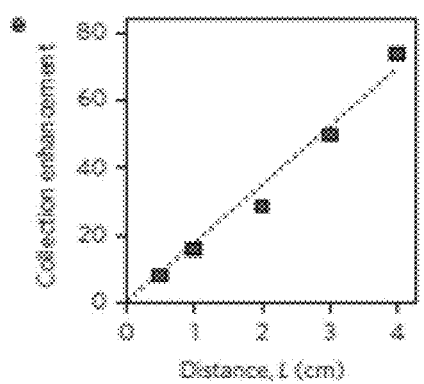
FIG. 10C is a plot illustrating a ratio of fluorescence measured with and without hydrogel bodies. Dashed line represents the linear regression ($R^2$=0.98)

Additional tests were performed to define the ability of the hydrogel body to collect light originated in the hydrogel body (for example, light produced by the sensory receptors 120 of FIG. 1) or light delivered to the hydrogel body from the surrounding tissue and to guide such collected light to a photodetector. To this end, what was measured was the amount of fluorescence light collected from a green fluorescent plate or dye solution (FITC; 5% wt/vol) over varying distances, with and without a hydrogel body lying between the sample and the fiberm as illustrated in FIG. 10A. The excitation light (at 455 mm) was delivered from a laser through the pigtail fiber 910. The length L of the hydrogel body in this experiment was varied by cutting it sequentially down from 40 mm to 30, 20, 10 and 5 mm. The light-collection efficiency of the optical fiber alone decreased according to $1/L^2$, while the light-collection efficiency of the hydrogel body followed a linear decay function of 1/L, FIG. 10B. The difference in ratio, or the enhancement factor, increased linearly with the length of the hydrogel, and was about 80-fold (19 dB) for 4-cm-long hydrogel bodies (FIG. 10C). These results demonstrate the desirable optical functions of the hydrogel bodies fabricated according to an embodiment of the invention, both in terms of transmitting light from an external source through the surface of the hydrogel body inside the hydrogel body and in terms of guiding light within the hydrogel body.

Cell-Encapsulation.

For demonstration of encapsulation of cells (such as, according to an idea of the invention, sensory receptors and reflex elements), Hela (human cervical cancer cell line) cells were mixed into the precursor PEGDA solution with Arg-Gly-Asp (RGD) peptides (1 mM), before crosslinking. Because of their refractive index profile (1.35-1.36 in the nucleus and 1.36-1.39 in the cytoplasm), the cells in the hydrogel body refract and scatter light propagating through the body.

Figure 10D:
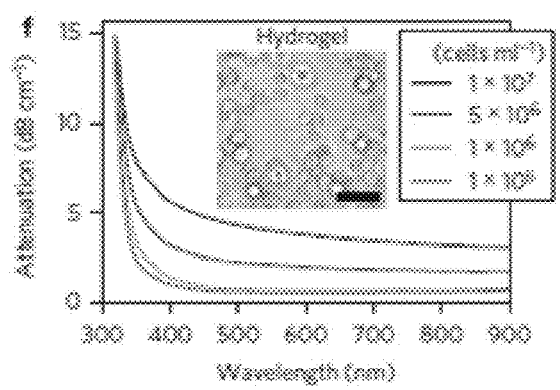
FIG. 10D is a plot showing optical attenuation spectra of hydrogel bodies corresponding to various spatial density of encapsulated cells. Inset: a phase-contrast micrograph of an embodiment of a hydrogel body. Scale bar, 50 mm.
Figure 10E:
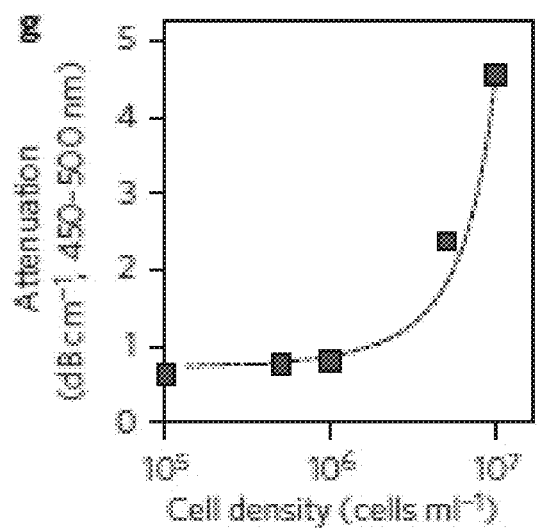
FIG. 10E is a plots depicting average optical attenuation of a hydrogel body encapsulating $1\times10^6$ cells/cm$^3$, in the spectral range 450-500 nm. Dashed line shows an exponential fit of experimental data points ($R^2$=0.96)

Absorption spectroscopy measurement was used to show light-scattering induced optical loss of cell-encapsulated hydrogel bodies, FIG. 10D. For a given cell density, the attenuation of light was relatively uniform over the visible to near-infrared range (400-900 nm), with slight decreases of attenuation with wavelength. The attenuation coefficients were found to increase nonlinearly with spatial density of the encapsulated cells, as shown in FIG. 10E, reaching the levels of about 2.4 dB/cm (Le=1.8 cm) for $5\times10^{-1}$ cells/ml in the spectral range 450-500 nm. The cell density of about $1\times10^6$ cells/ml was determined to be optimal for 4-cm-long hydrogels, for which optical loss is less than 1 dB/cm as the 1/e attenuation length (Le=5.6 cm) is comparable to the length of the hydrogel body itself. At this cell density, a hydrogel with dimensions of $1\times4\times40$ mm$^3$ (volume of about 0.16 cm$^3$) could contain up to 160,000 cells and, without molecular absorption, carry 70% of the light to its distal end.

Verification of Operation of an Embodiment in Conjunction with Biological Tissue.

Juxtaposition of a Cell-Containing Hydrogel Body with the Tissue.

In one group of experiments, hydrogel bodies (FIG. 1, containing embodied therein sensor cells) were implanted into a subcutaneous pocket in mice through a 1-cm-long skin incision on the back. The pigtail fibers were securely cemented onto the skull to establish stable light coupling to the hydrogel while the animal was awake and moving freely. Light leaking out of a hydrogel body (FIG. 11A) to the surrounding tissue could be readily monitored with a photodetector through the thin skin layer. As shown in FIG. 11C, the optical intensity throughout the entire implant (shown as area 1110) varied by no more than 6 dB, which is slightly higher than the 1 dB/cm measured in air and is due to the contact with the tissue (index, 1.34-1.41). By comparison, when only a multimode fiber was implanted without a hydrogel body, FIG. 11B, the 1/e light intensity was constrained to a small region 1120 with a diameter of 2-3 mm as seen through the skin. This result represents a 40-fold increase of the illumination area with the light-guiding scaffold.

The hydrogel bodies and surrounding tissues were harvested at days 3 and 8 after implantation (n=3). Fluorescence microscopy measurement complemented with cell viability probes showed that about 80% of the embedded cells were found live in the hydrogel bodies in vitro after photocrosslinking, and more than 70% and 65% of the embedded cells in the implanted hydrogel bodies remained viable after 3 and 8 days (FIG. 11D, a), respectively, which was consistent with measurements with hydrogels in a culture dish in vitro (FIG. 11D, b). The decrease in optical transmittance values T at 3 and 8 days in vitro and in vivo were less than 1 dB/cm (FIG. 11E).

Figure 11F:
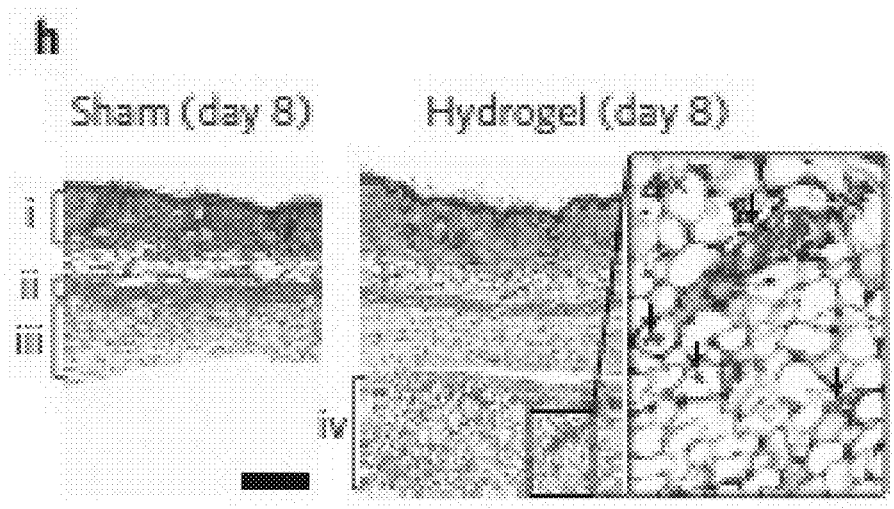
FIG. 11F presents H&E histology images of skin tissues examined 8 days after implantation: (i) dermis, (ii) panniculus carnosus, (iii) subcutaneous loose connective tissue layer and (iv) newly formed connective tissue layer. In the 4× magnified image (right), arrows indicate red blood cells in blood vessels. Scale bar, 100 mm.
Figure 12A:
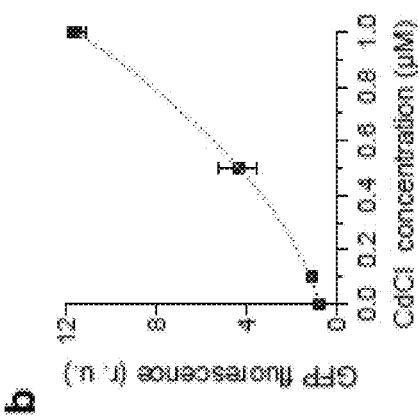
FIGS. 12A, 12B, 12C, and 12D: Experimental illustration of activation of heat-shock protein (hsp70) gene in response to cadmium ions.
Figure 12B:
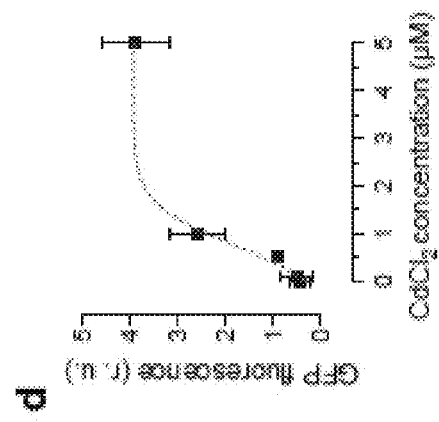
Figure 12C:
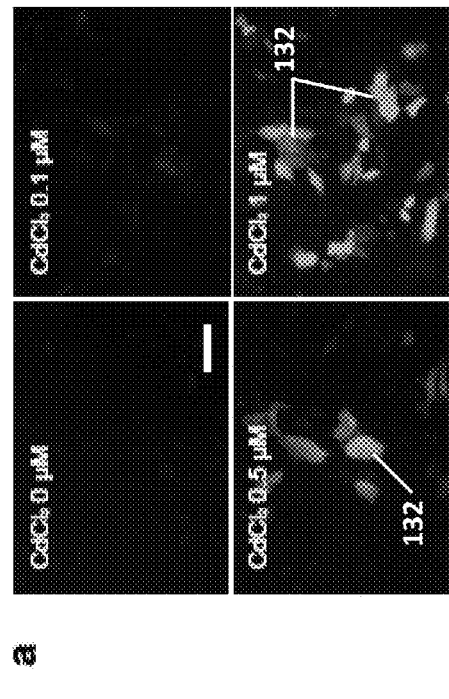
Figure 12D:
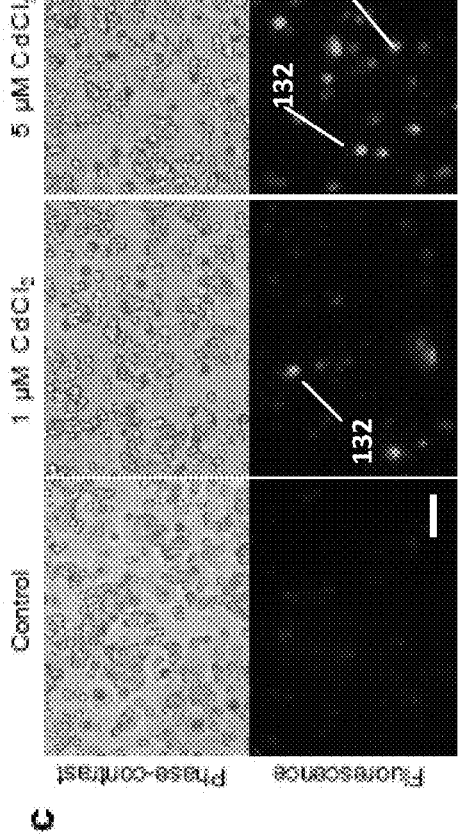
Figure 13:
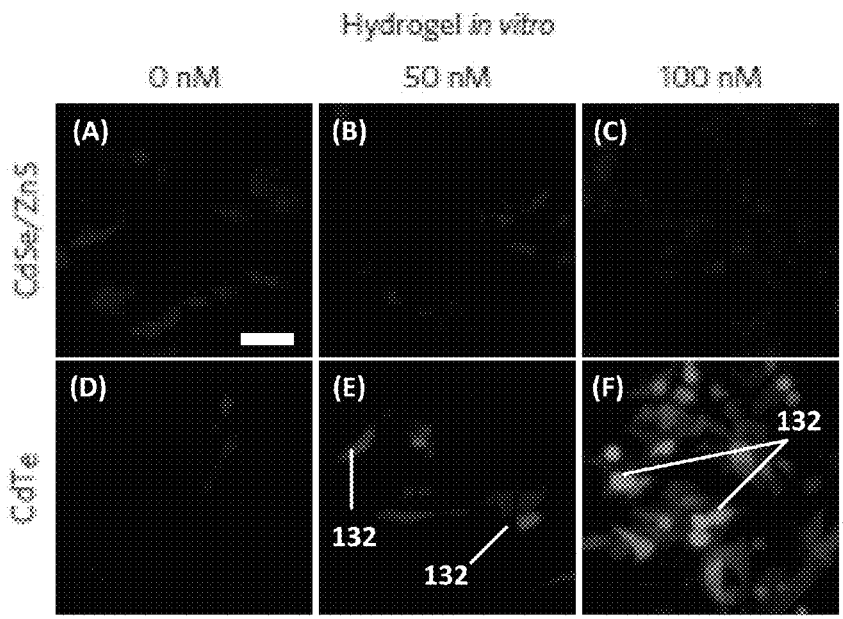
FIGS. 13A, 13B, 13C, 13D, 13E, and 13F: Optical images of sensor cells encapsulated in hydrogel bodies in vitro, two days after adding CdTe (FIGS. 13D, 13E, 13F) or CdSe/ZnS (FIGS. 13A, 13B, 13C) quantum dots into the tissue. Scale bar, 20 mm.
Figure 14:
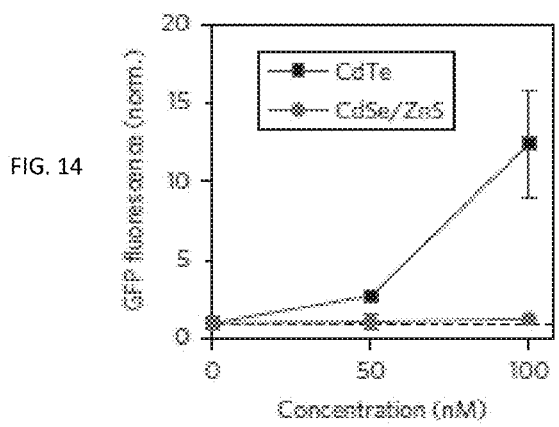
FIG. 14 is a plot illustrating magnitude of green fluorescence collected from the hydrogel body through the pigtail fiber and detected with an optical detector of the embodiment of FIG. 3.

Histological experiments suggested there were no major immune-cell infiltrations, but the formation of connective tissues around the implants, which is a typical mild reaction to foreign bodies, was observed in all, but not in shamsurgery, animals (FIG. 11F). The newly formed tissues were moderately vascularized. The hydrogel implants as a whole came off the surrounding tissues easily during tissue collection, indicating a lack of adhesion between the tissues and hydrogels.

Detection of Nanotoxicity.

In a related group of experiments, using the embodiments of FIGS. 1, 2 and 3, fiber-optically pigtailed cell-containing hydrogel bodies were implanted in a tissue for the measurement of the toxicity caused by quantum dots at the tissue. To sense cellular toxicity, elements of an intrinsic cellular cytotoxicity sensor-heatshock-protein 70 (hsp70)—which is activated when tissue cells are under cytotoxic stress (such as from heavy metal ions and reactive oxygen species) were used as reflex elements 220 embedded in the hydrogel body. Sensor receptors 120 were formed from elements of a green fluorescent protein (GFP) material under the hsp70 promoter.

In reference to FIGS. 12A, 12B, 12C, and 12D, $CdCl_2$ elements were brought into contact with the tissue. Cadmium can cause cytotoxic effects when released as a result of degradation of the quantum dots. The sensor cells 120 in vitro irradiated with the excitation light 130 emitted fluorescent light 132, the power of which increased when the dose of $CdCl_2$ was elevated to 1 mM, but saturated at higher concentrations of 1-5 mM.

In a related group of experiments, two types of cadmium-containing quantum dots were tested: core-only CdTe and core/shell CdSe/ZnS nanoparticles. The sizes of the bare and shelled quantum dots were chosen to be about 3.2 nm and 5.2 nm, respectively, so they emit red light (at about 605 nm) that is easily distinguishable from the green fluorescent signal emitted by the sensory receptor cells 120. When the cells 120 were encapsulated in a hydrogel in vitro, the sensor optical signal 132 increased with the concentration of CdTe quantum dots in the tissue. IN contradistinction, no noticeable change of green fluorescence 132 was observed when CdSe/ZnS quantum dots were used (FIGS. 13A, 13B, 13C, 13D, 13E, 13F, and 14). These results confirmed the role of the ZnS shell in reducing cellular toxicity.

Figure 15:
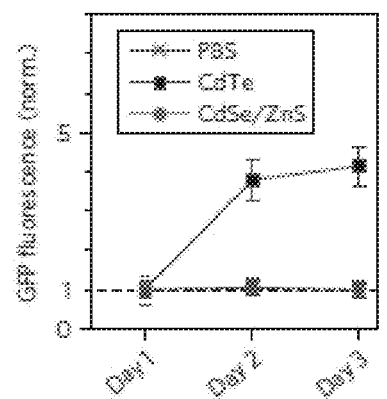
FIG. 15 is a plot illustrating results of an in vivo measurement of fluorescence produced by the sensing cells (encapsulated in hydrogel bodies, which were implanted in live tissue according to an embodiment of the invention) in response to a toxin produced by quantum dots that were administered by intravenous injection 24 h after the hydrogels were implanted.
Figure 16:
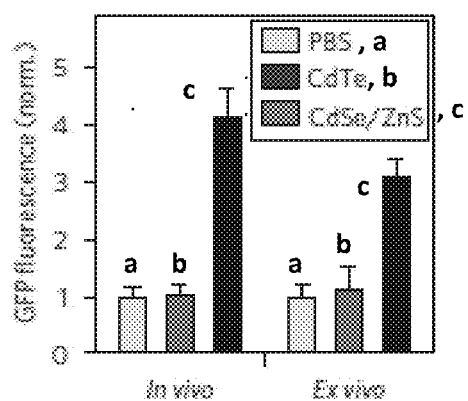
FIG. 16 is a chart representing comparison of GFP fluorescence signals produced by sensory receptors and collected through a fiber-pigtail in vivo and by fluorescence microscopy ex vivo.

In a related group of experiments, three groups of living tissue (mice) were implanted with cell-encapsulating hydrogel bodies. The living tissues were treated by a systemic injection of CdTe quantum dots (100 pM), CdSe/ZnS quantum dots (100 pM), and PBS only (the latter being a control group). Time-lapse fiber-optic fluorescence measurement performed with the use of the embodiment of FIG. 3 showed a significant increase in green fluorescence 132 in the CdTe-treated group of tissue, but not in the CdSe/ZnS-treated and control groups, at days 1 and 2 after treatment; FIG. 15. To validate this measurement, the hydrogel implants were extracted at day 2 and examined with the use of fluorescence microscopy. The total magnitude of GFP fluorescence from the cells was qualitatively consistent with the values measured in situ in live mice (FIG. 16). These results represent the first real-time measurement of systemic cellular toxicity by cadmium-based quantum dots and the effect of surface capping by biocompatible shells.

Optogenetic Therapy of Diabetic Living Tissue.

Figure 17A:
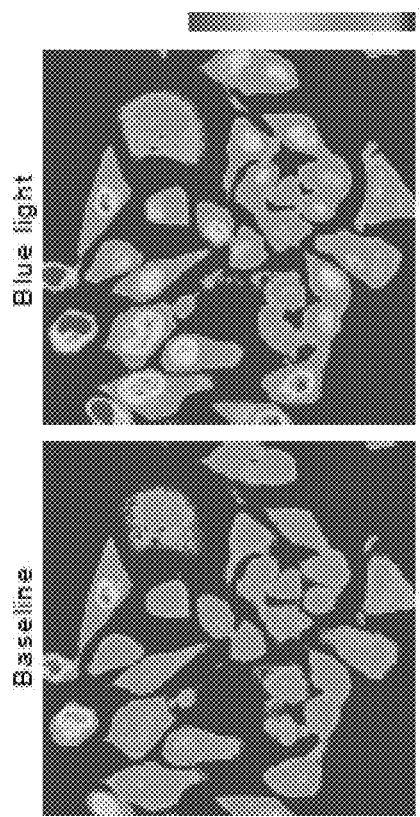
FIGS. 17A, 17B, 17C, and 17D illustrate experiments with stable cell line for light-induced GLP-1 secretion, produced with two plasmids named pHY42 (human melanopsin) and pHY57 (NFAT promoter driven GLP-1 expression).
Figure 17B:
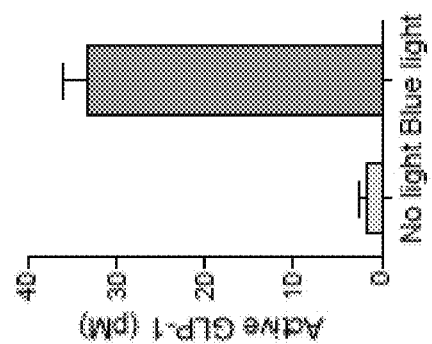
Figure 17C:
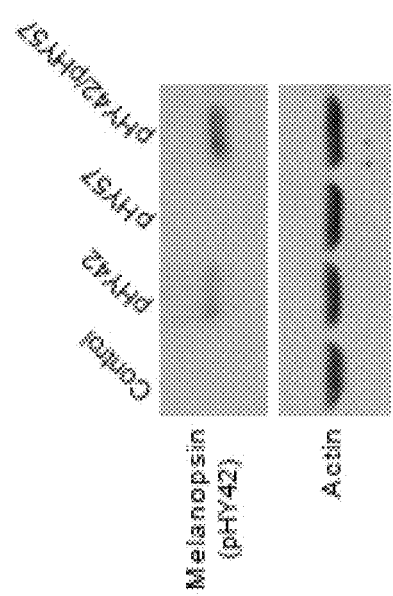
Figure 17D:
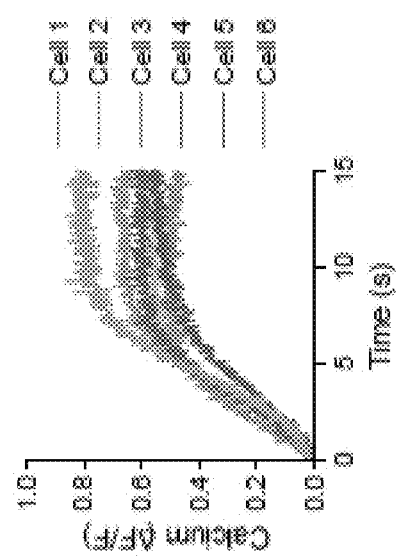

To demonstrate cell-based therapy we used a vector construct previously developed for optogenetic synthesis of GLP-19 and generated a stably transfected cell line, FIGS. 17A, 17B, 17C, and 17D. Following absorption of blue light, the light-responsive protein melanopsin is activated in the plasma membrane, which increases intracellular calcium and consequently activates a transcription factor (nuclear factor of activated T cell, NFAT), which drives the production of GLP-1. GLP-1 is an antidiabetic secretory protein that promotes glucose homeostasis by stimulating glucose-dependent insulin secretion. The intended function of these optogenetic cells (encapsulated in a hydrogel in vitro) was initially confirmed. To monitor the change in the intracellular calcium level, the optogenetic cells were loaded with a fluorescence-based calcium indicator (OGB1-AM). More than 80% of the cells illuminated by blue light showed an increase of intracellular calcium within several seconds (FIGS. 17A, 17B). The enzyme-linked-immunosorbent assay (ELISA) on the media (in which the cell-encapsulated hydrogels were immersed) was performed and a significant increase of GLP-1 concentration in the light-exposed (on) samples compared to non-illuminated (off) controls (FIG. 17C) was detected. These result confirmed the optogenetic synthesis of GLP-1 and the permeability of secreted GLP-1 molecules through the crosslinked hydrogel.

To further investigate the therapeutic potential of the optogenetic polymer hydrogel based system, cell-containing hydrogel bodies (such as the body 110) were implanted into mice with chemically-induced diabetes, FIGS. 18A, 18B, 18C, 18D, 18E. With the use of an embodiment of the external opto-electronic system of FIG. 3, blue light 234 (455 nm, 1 mW) was delivered to the hydrogel body for 12 h after implantation. At 48 h after implantation, light-exposed animals (n=4) showed an approximately twofold increase in the blood GLP-1 level compared to the non-illuminated control group (FIG. 18D). To validate physiological efficacy, a glucose tolerance test was performed. Following an intraperitoneal injection of glucose (1.5 g/kg), the light-treated group achieved significantly improved glucose homeostasis, with the blood glucose level returning to the initial level of 14 mM in 90 min (FIG. 18E). In contrast, the blood glucose level of the non-treated group remained higher than 28 mM, even after 120 min (FIG. 18E). These results demonstrate the therapeutic potential of the cell-embedding hydrogel implant, configured according to an embodiment of the invention, for optically controlled optogenetic synthesis in the body.

Discussion

Interest in developing photonic devices employing biomaterials (such as silk fibroin, agar, and synthetic polymers, for example), has been growing. Biocompatible photonic components, such as optical fibers and gratings, have been demonstrated, and their optical functions have been tested in in vitro and, to some extent, in vivo settings. The experimental results disclosed here demonstrate for the first time the use of PEG-based hydrogels in vivo biomedical applications of cell-containing polymer hydrogel lightguides that can be configured not only as a cellular scaffold but also as a bidirectional optical communication channels for cells encapsulated therein. Optical hydrogel bodies configured as tissue implants encapsulating cells with luminescent reporters and optogenetic gene-expression machinery demonstrate real-time sensing of nanotoxicity in living tissue and also optogenetic diabetic therapy with optical powers on the order of only 1 mW (which is much more efficient than conventional transdermal delivery).

Optical transparency is essential for most photonic applications of hydrogels. We found that the longer PEGDA polymers yielded a higher transparency after crosslinking. This general tendency may be explained by the formation of pores in crosslinked hydrogels. In solutions before crosslinking, the precursor PEG chains are homogeneously dispersed in water and, therefore, transparent. Ultraviolet-induced polymerization reorganizes the monomer distribution following energy minimization. This can introduce spatial inhomogeneity depending on the molecular compositions and crosslinking parameters. As a distinct phenomenon, phase separation between the polymer-rich phase and the water-rich phase can occur when the water content exceeds the maximum equilibrium level the crosslinked polymer can take up during polymerization. The resulting pores, with sizes ranging from nanometers to micrometers, cause light scattering due to the refractive index contrast, and reduce the transparency of the hydrogel. This mechanism explains the opaqueness of 0.5 kDa PEG hydrogels made at 10% wt/vol and the improved transparency at lower water contents (higher concentrations 0.15% wt/vol) disclosed above.

The light-guiding properties of hydrogel assemblies fabricated according to an embodiment of the invention can be tailored for specific requirements by controlling the shape and structure of the hydrogel body. For example, cell-based therapy in patients would require a sizable hydrogel body containing a large number of cells (for example, over $10^9$ cells for human patients; over $10^6$ cells in animal patients) so as to produce a physiologically relevant dose. In this case, a hydrogel body can be structured with an additional cladding layer of a lower refractive index to enhance lightguiding. The width of the hydrogel body may be tapered to compensate for cell-induced optical loss and thereby obtain a more uniform optical intensity throughout the entire volume of the body. Besides PEG, other polymers such as hyaluronic acid, alginate and collagen, for example, are good candidates for optical hydrogel for implementing an embodiment of the invention. Hydrogels based on these polymers have shown excellent properties for cell encapsulation. Compositional screening and optimization for optical characteristics could result in a range of material options for light-guiding hydrogels with different refractive indices. Other than a preformed hydrogel, injectable hydrogels such as thermo-responsive gels, such as PEG-PLGA-PEG triblock copolymer, may be used to facilitate minimally invasive implantation via in situ gelation. Optimization of mechanical stability, flexibility or biodegradation can be facilitated by modifying the chemical compositions or fabrication protocol (by, for example, controlling the gelation time). Additionally, a photodegradable group such as photodegradable acrylate may be introduced to control biodegradation kinetics.

Collected empirical data indicate that increase of the spatial density of cells encapsulated in a hydrogel body according to an embodiment can be increased up to at least ($5\times10^6$ cells/cm$^3$) without lowering the optical transmission substantially, and even higher concentrations may be possible with optimized hydrogel designs. Furthermore, different host cells with enhanced transfection efficiency may be used. For example, HEK293 cells have an order-of-magnitude higher protein production rate than the Hela cells used in our work. Additionally, genetic and protein engineering to increase the production rate and stability of therapeutic proteins will allow a further reduction in implant size.

The cell-encapsulating hydrogel implant should be functionally stable in vivo for several weeks and months depending on the application (for example, for chronic problems). While such a long lifetime is currently challenging, it is not unattainable.

The light-guiding hydrogel system can also make use of non-cell-based chemical sensors and photoactive therapeutic molecules. Although this alternative approach does not necessarily benefit from the unique features (such as self-sustainability) that the cells provide, it is simpler and allows existing molecular probes and drugs to be used in conjunction with light-guiding hydrogels.

In accordance with examples of embodiments, described with reference to FIGS. 1-18, a new polyethylene glycol-based hydrogel lightguide-based system was demonstrated that embeds the first cells configured as a user-triggered sensor of a stimulus generated by ambient with which the hydrogel is juxtaposed, and second cells configured as emitters of physical or chemical output for interaction with the ambient. The polymer hydrogel lightguiding body offers excellent low-loss (<1 dB/cm) light-guiding properties and simultaneously meets all practical requirements, including long-term cell encapsulation, biocompatibility, mechanical flexibility and long-term transparency in vivo. By coupling numerous cellular sensing and secretary protein-production pathways (sensory receptors and reflex elements, or first and second cells) with optical readout and optogenetic signalling, the optical hydrogel-based system may serve as a platform technology with a broad range of applications in diagnosis and therapy. In particular, using optogenetic, glucagon-like peptide-1 (GLP-1) secreting cells, light-controlled therapy using the hydrogel in a mouse model with diabetes was conducted, and improved glucose homeostasis was attained. Furthermore, real-time optical readout of encapsulated heat-shock-protein-coupled fluorescent reporter cells made it possible to measure the nanotoxicity of cadmium-based bare and shelled quantum dots (CdTe; CdSe/ZnS) in vivo.

While the invention is described through the above-described examples of embodiments, it will be understood by those of ordinary skill in the art that modifications to, and variations of, the illustrated embodiments may be made without departing from the inventive concepts disclosed herein. For example, various sensory receptors (sensing cells) can be employed in an embodiment of the invention, such as sensor cells made by genetically introducing a reported gene into a host cell. The reporter gene includes (1) promoter configured to sense environmental change and turn on or off the coupled protein expression and (2) optical reporter protein that is either fluorescent or luminescent:

(i) cells can be genetically engineered to express optical reporters (for example, green fluorescent protein, yellow fluorescent protein, red fluorescent proteins, and so on) in response to specific physiologic changes;

(ii) cytotoxic stress sensing cell (such as a discussed above heat-shock-protein-70 activated when there is cytotoxic stress—such as heavy metal ions, heat, or reactive oxygen species—is present; or a cell represented by the chemical formula A=X—O2). This arrangement can be used in monitoring of tissue intoxication. In mammalian cells a temperature change on the order of 1 degree C. can introduce a heat-shock response; change in protein structure can cause activation of the cells; (iii) hypoxia (lack of oxygen) sensing cell, operating with the use of the HIF (hypoxia-inducible-factor) promoter (in one specific example—the HSP70-GFP discussed above); threshold can be different dependent on the location of such cell, but generally oxygen tension lower than 5 mmHg can be considered as hypoxic;

(iv) glucose sensing cell (in which case glucose-susceptible fluorescent probe is loaded into the cell); see, for example, Kawanishi in J. of Fluorescence, Vol. 14, no. 5, September 2004 mentioned above or Heo et al., PNAS, Aug. 16, 2011, vol. 108, no. 33, pp. 13399-13403, the disclosure of each of which is incorporated herein by reference;

Reflex elements (or second cells) for use in a hydrogel body can be formed, for example, by genetically introducing light-responsive protein (i.e. optogenetic material) and additional genetic engineering of downstream signaling, or cells that secrete therapeutic agents (e.g. hormones) in response to light, such as, for example: (a) Insulin-secreting cells (to reduce blood glucose level) as a consequence of detection of an elevated level of glucose with the glucose-sending first cells in the hydrogel body and in response to excitation light; (Transfect melanopsin introduced to pancreatic beta cells. Then the pancreatic beta cells can secrete insulin in responsive to blue light (400-500 nm) due to increase of intracellular calcium by melanopsin, when exposed to light and the intracellular calcium triggers release of insulin hormone);

(b) Glucagon-secreting cells (to raise concentration of glucose in the bloodstream). GLP-1 (enhance glucose homeostasis) cells. (Example: Transfect melanopsin and NFAT-GLP1 genes introduced a cell such as a cervical cancer cell line, HeLa. Then light increases intracellular calcium level, the calcium activates NFAT transcription factor, and triggers gene expression of the GLP-1. GLP-1 will be released from the cells to improve glucose homeostasis. In one implementation, the illumination protocol includes irradiance of 1 mW/cm$^2$, 5 sec on-5 sec off cycles, exposure duration of 3-12 hours).

Such sensor cells or therapeutics cells can be used in combination and separately controlled by using different optogenetic machineries responding to light of different wavelengths.

It is understood, therefore, that various light-sensitive molecules and genetic engineering tools can be used to create optical interfaces into cells. Fluorescent or bioluminescent proteins can be integrated in a specific pathway of endogenous sensing machinery for highly selective sensing. Photo active proteins, such as channel rhodopsin and melanopsin, can be coupled with the pathway leading to light-driven production of a therapeutic substance, while controlling the timing and dose of such production with light.

The overall principle of design of sensory/reflex cells is as follows: Cells are made via genetic engineering procedure. First, most cells are naturally nonresponsive to light so a gene is introduced that encodes a protein that has light responsiveness (e.g. channelrhodpsin: ion channel that only opens when light is illuminated or melanopsin: a G-protein-coupled receptor responsive to light). The absorption spectra of currently available light-responsive proteins range from violet to far-red depending on its subtype. The cells open an ion channel (in case of channelrhodopsin) or increase intracellular calcium ion level (in case of melanopsin). Then, the ion messengers are linked to gene expression (e.g. NFAT-GLP-1) or protein secretion (e.g. insulin, glucagon).

Figure 19:
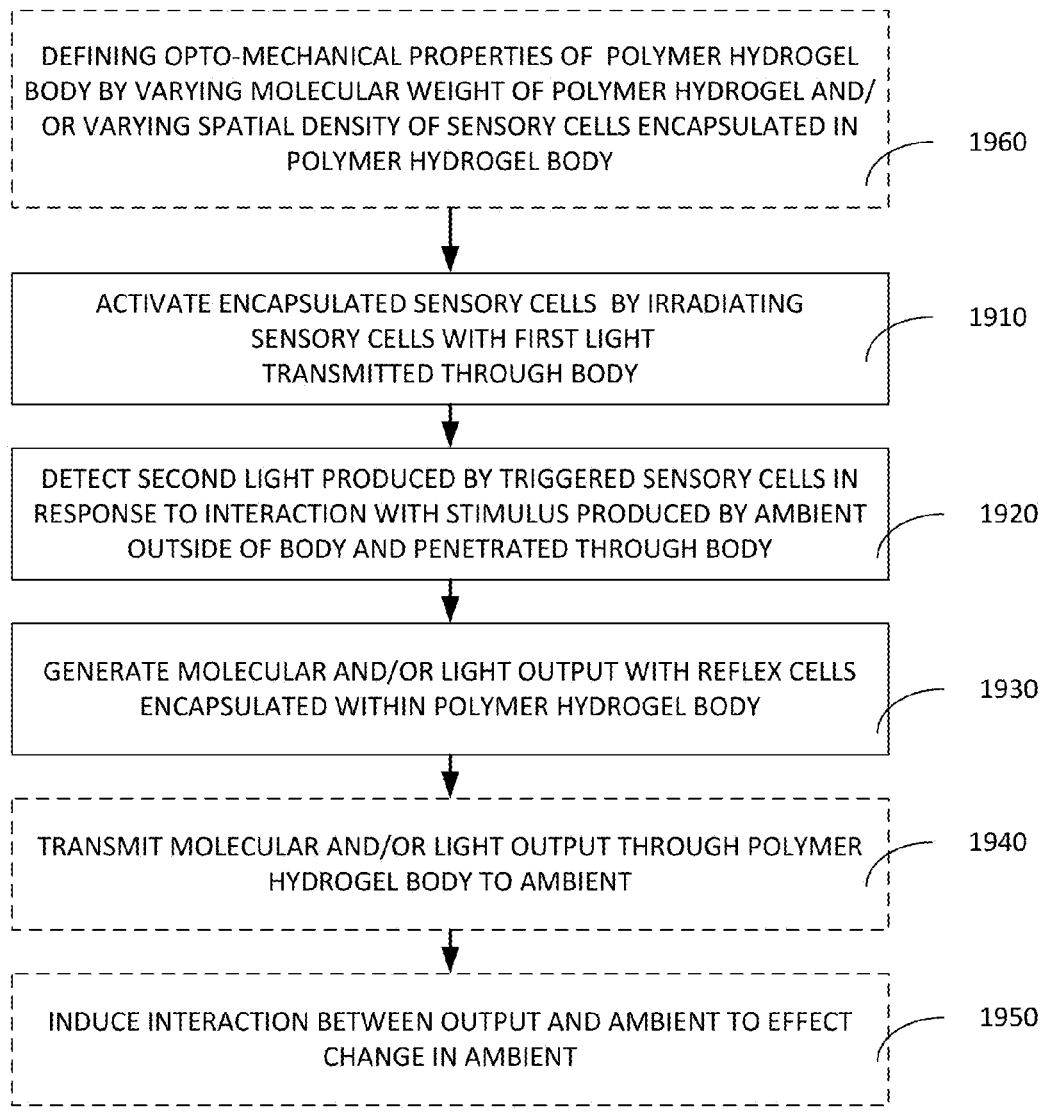
FIG. 19 is a flow-chart illustrating an embodiment of a method of the invention.

FIG. 19 presents a flow-chart illustrating schematically an embodiment of a method of the invention. According to one implementation, at step 1910 the sensory cells incorporated (embedded) in a polymer hydrogel body of an assembly of the invention are irradiated with triggering light to be rendered sensitive to a stimulus signal that is originated by ambient outside of the hydrogel body and to generate light in response to having interacted with such stimulus. As a result of detection of light generated by sensory cells at step 1920, the determination of a characteristic of at least one of the stimulus and the ambient is made with electronic circuitry (that may include a programmable processor) operably cooperated with the assembly. As a result of such determination, a conclusion is made whether to activate the reflex cells (also encapsulated within the polymer hydrogel body) with yet another light input that is initiated from outside of the hydrogel body and is delivered through and by the hydrogel body to the reflex cells. In response to such activation, the reflex cells are caused to generate a material output (by emitting a molecule of chemical substance or light) at step 1930, which output may be optionally delivered through the hydrogel body to the ambient at step 1940 to induce interaction with the ambient, at step 1950 with a purpose of affecting a characteristic of the ambient. The opto-mechanical properties of the polymer hydrogel body (such as optical transmittance and/or scattering and/or mechanical flexibility) can be optionally controlled, at step 1960, by varying molecular weight of the polymer used in formation of the polymer body of the assembly and/or varying spatial density of cells embedded in it.

Disclosed aspects, or portions of these aspects, may be combined in ways not listed above. Accordingly, the invention should not be viewed as being limited to the disclosed embodiment(s).

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

In addition, when the present disclosure describes features of the invention with reference to corresponding drawings (in which like numbers represent the same or similar elements, wherever possible), the depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, at least for purposes of simplifying the given drawing and discussion, and direct the discussion to particular elements that are featured in this drawing.

The invention as recited in claims appended to this disclosure is intended to be assessed in light of the disclosure as a whole, including features disclosed in prior art to which reference is made.

Process of light-based excitation of encapsulated cells and/or detection of optical signals generated by sensory cells in embodiments of the inventions has been described as including a processor controlled by instructions stored in a memory. The memory may be random access memory (RAM), read-only memory (ROM), flash memory or any other memory, or combination thereof, suitable for storing control software or other instructions and data. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks.

In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

What is claimed is:

1. An assembly, comprising:
a polymer hydrogel body;
sensory receptors encapsulated inside said body, said sensory receptors configured:
when irradiated with first light channeled thereto by said body, to detect a stimulus produced by an ambient in the vicinity of said body, and
to emit second light is response to a detection of said stimulus;
and
reflex elements encapsulated inside said body, said reflex elements configured
in response to user input applied thereto, and following emission of said second light by said sensory receptors, to generate an output configured to interact with said ambient.

2. An assembly according to claim 1, wherein said sensory receptors are distributed inside said body with spatial density of at least $1*10^6$ cells per cubic centimeter.

3. An assembly according to claim 1, wherein said polymer hydrogel body has optical transparency that, as a chosen wavelength, increases with increase in molecular weight of a hydrogel contained in said polymer hydrogel body.

4. An assembly according to claim 1, wherein said polymer hydrogel body has mechanical flexibility that increases with increase in molecular weight of a hydrogel contained in said polymer hydrogel body.

5. An assembly according to claim 1, having a scattering-induced attenuation of light propagating therethrough that is increases non-linearly with increase of spatial density of said sensory receptors encapsulated within said polymer hydrogel body.

6. An assembly according to claim 1, wherein said reflex elements are configured to generate said output only when irradiated with third light delivered thereto through said polymer hydrogel body.

7. An assembly according to claim 1, further comprising a source of light and an optical detection unit in optical communication with said polymer hydrogel body.

8. An assembly according to claim 7, further comprising an optical waveguide connecting said source of light and said polymer hydrogel body.

9. An assembly according to claim 7, further comprising a programmable processor operably connected with said source of light and said optical detection unit and configured to govern operation thereof.

10. An assembly according to claim 7, wherein said source of light is embedded in said polymer hydrogel body.

11. An assembly according to claim 1, further comprising programmable electronic circuitry configured to cause generation of
(i) said first light by a source of light and
(ii) data, representing a characteristic of the stimulus based on second light received by an optical detection,
said source of light and optical detection unit disposed outside of said polymer hydrogel body in optical communication with said sensory receptors and reflex elements.

12. An assembly according to claim 1, wherein said output includes at least one of a molecule and a photon of light.

13. A method for operating an assembly, the method comprising:
- transmitting first light through a polymer hydrogel body, of the assembly, to activate sensory receptors encapsulated in said body to render said sensory receptors sensitive to a stimulus produced outside of said polymer hydrogel body;
- detecting second light, generated by activated sensory receptors in response to said stimulus, with an optical detection unit of the assembly; and
- generating an output with reflex elements encapsulated within said polymer hydrogel body, said output including one or more of a molecular output and a photon output.

14. A method according to claim 13, wherein said transmitting includes guiding said first light, which has been externally delivered to said body, within said body.

15. A method according to claim 13, wherein said transmitting includes transmitting first light through said polymer hydrogel body subcutaneously implanted into a biological tissue.

16. A method according to claim 13, wherein said transmitting includes transmitting of light through a polymer hydrogel body having absorption, of said light, that is non-linearly dependent on a spatial density of said first cells encapsulated therein.

17. A method according to claim 13, further comprising transmitting at least one of said stimulus and second light through said body.

18. A method according to claim 13, further comprising defining optical transmittance of said polymer hydrogel body by varying molecular weight of a polymer hydrogel contained therein.

19. A method according to claim 13, further comprising delivering said second light to a detector outside of said tissue, wherein said transmitting includes transmitting first light delivered to said body from a light source disposed outside of said tissue.

20. A method according to claim 13, wherein said generating includes generating second light in response to a stimulus produced by an ambient biological medium exposed to toxic environment, and wherein said generating includes generating second light indicative of the presence of an antidote in said toxic environment.

21. A method according to claim 13, further comprising transmitting said output outside of said polymer hydrogel body.

* * * * *